United States Patent [19]

Issachar

[11] Patent Number: 5,156,972
[45] Date of Patent: Oct. 20, 1992

[54] ANALYTE SPECIFIC CHEMICAL SENSOR WITH A LIGAND AND AN ANALOGUE BOUND ON THE SENSING SURFACE

[75] Inventor: David Issachar, Rehovot, Israel
[73] Assignee: The State of Israel, Atomic Energy Commission, Soreq Nuclear Research Center, Yavne, Israel
[21] Appl. No.: 577,744
[22] Filed: Sep. 5, 1990

[30] Foreign Application Priority Data

Sep. 5, 1989 [IL] Israel .......................................... 91526
Jan. 3, 1990 [IL] Israel .......................................... 92955

[51] Int. Cl.⁵ ........................ C12M 1/40; C12M 1/34; G01N 27/26
[52] U.S. Cl. .................................... 435/288; 435/291; 435/808; 435/817; 422/82.01; 422/82.06; 422/82.11; 204/403
[58] Field of Search ....................... 435/7.93, 288, 808, 435/817, 287, 291; 422/82.01–82.08; 204/403

[56] References Cited

U.S. PATENT DOCUMENTS

| | | | |
|---|---|---|---|
| 3,838,011 | 9/1974 | Hagen et al. | 436/52 |
| 4,443,407 | 4/1984 | Weinberg et al. | 436/52 |
| 4,795,707 | 1/1989 | Niiyama et al. | 435/288 |
| 4,822,566 | 4/1989 | Newman | 422/82.01 |
| 4,880,752 | 11/1989 | Keck et al. | 435/288 |
| 4,916,075 | 4/1990 | Malmros et al. | 435/288 |
| 4,973,561 | 11/1990 | Hansen et al. | 436/52 |
| 4,978,503 | 12/1990 | Shanks et al. | 435/288 |

OTHER PUBLICATIONS

"A Minature Optical Glucose Sensor Based on Affinity Binding", S. Mansouri, J. Schultz; *Bio/Technology*, pp. 885–890 (Oct. 1984).
"Fiber-Optic Biosensors Based on Fluorescence Energy Transfer", D. Meadows, J. Schultz; *Talanta*, vol. 35, No. 2, pp. 145–150 (1988).
"Fiber Optic Immunochemical Sensor for Continuous, Reversible Measurement of Phenytoin", P. Anderson, G. Miller; *Clinical Chemistry*, vol. 34, No. 7, pp. 1417–1421 (1988).
"Monoclonal Antibody Biosensor for Antigen Monitoring"; D. Bush, G. Rechnitz; *Analytical Letters*, vol. 20, No. 11, pp. 1781–1790 (1987).
"Fiber-Optic Chemical Sensors for Competitive Binding Fluoroimmunoassay"; B. Tromberg, et al., *Analytical Chemistry*, vol. 59, pp. 1226–1230 (1987).
"Recent Advances in the Development and Analytical Applications of Biosensing Probes", Arnold et al.; *CRC Critical Reviews in Analytical Chemistry*, vol. 20, Issue 3, pp. 149–196 (1988).
"Regenerable Fiber-Optic-Based Immunosensor", F. Bright, T. Betts, K. Litwiler; *Analytical Chemistry*, vol. 62, No. 10, pp. 1065–1069 (May 1990).
"Fiber Optic Sensors: Recent Developments", M. Abdel-Latif, A. Suleiman, G. Guilbault; *Analytical Letters*, vol. 23, No. 3, pp. 375–399 (1990).

Primary Examiner—James C. Housel
Assistant Examiner—William Chan
Attorney, Agent, or Firm—Foley & Lardner

[57] ABSTRACT

An analyte specific chemical sensor for determining an analyte in a test medium. The sensor comprises a sensing surface which is coated with reversible competitive recognition units (RCRUs) each of which contains as constituent components at least one receptor and at least one ligand, one of which components is an analyte analogue. In these RCRUs the receptor and the ligand are a priori connected to each other, directly or indirectly, in such configuration that even when, for example, an analyte analogue ligand is displaced from the receptor by an analyte ligand, the analogue will still be retained in relatively close proximity to the receptor. In addition, the relative positions of the receptor and the ligand in the RCRU are such that when no analytes are present or when the analyte concentration is at a low level, they are affinity conjugated by a specific affinity interaction. The fluctuations of analyte concentrations in the test sample affect the chemical occurrences at the RCRUs, and consequently the physico-chemical characteristics of its components. The changes in the analyte concentration are monitored, according to the present invention, by continuously measuring the changes of the above physico-chemical characteristics induced by occurrences at the RCRUs, namely inner association and dissociation. Such physico-chemical characteristics may be, for example, photochemical, e.g. light absorption, light emission, light scattering and light polarization; electrochemical; and piezoelectrical.

25 Claims, 30 Drawing Sheets

Preparation of Solid-Phase Reversible System of Fig. 2(a)
Ab = antibody
Ag* = labelled antigen
M1, M2 = bifunctional spacer molecules
(i) Preparation of the appropriate derivatives
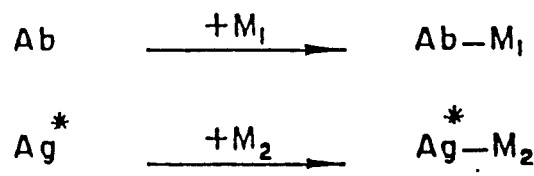
(ii) Conjugate preparation
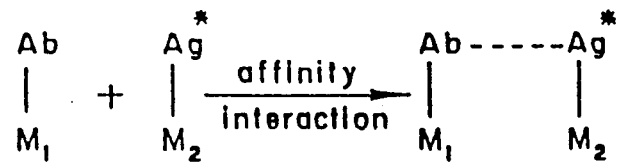
(iii) Immobilization on the surface
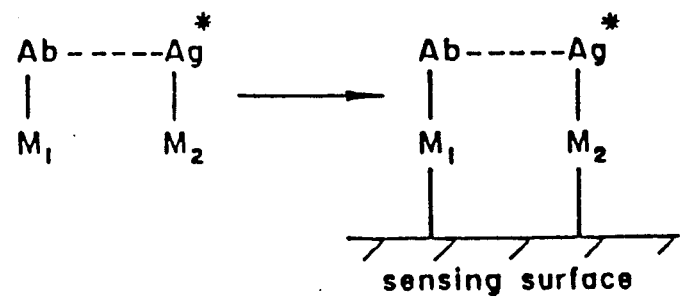
FIG. 8

Preparation of Solid-Phase Reversible Immunosensor of Fig. 2(c)

Polyala = DL-Polyalanine
X, Y = functional groups
M = spacer molecule (i) Immobilization of bis-(DL-polyalanine) spacer on the sensing surface to get:

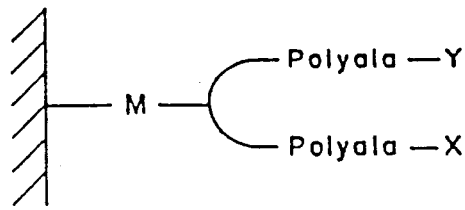

(ii) Binding Ag* on one of the long spacers to get:

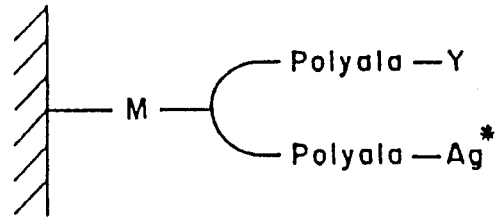

(iii) Affinity induction with the specific Ab to get:

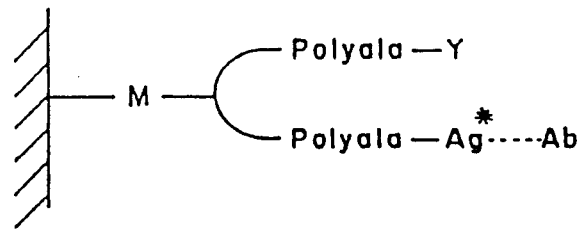

(iv) Covalent binding of the Ab with the other polyala spacer to get:

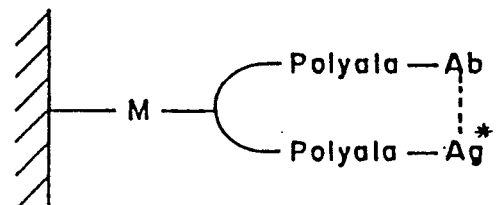

FIG. 9

Preparation of Solid-Phase Reversible System of Fig. 2(d)
StAv = Streptavidin
B = Biotin
M = Spacer molecule
(i) Immobilization of Streptavidin to the Sensing surface
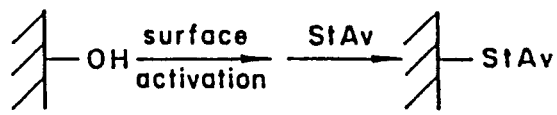
(ii) Biotinylation of the labelled antigen Ag*
(iii) Biotinylation of the antibody Ab
Ab + M—B ⟶ Ab—M—B
(iv) Immuno conjugate production
(v) Immobilization of the Immuno Conjugate to the Sensing surface
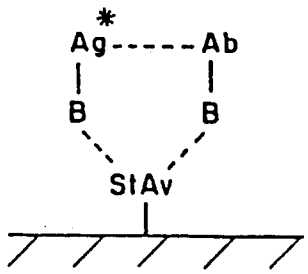
FIG. 10

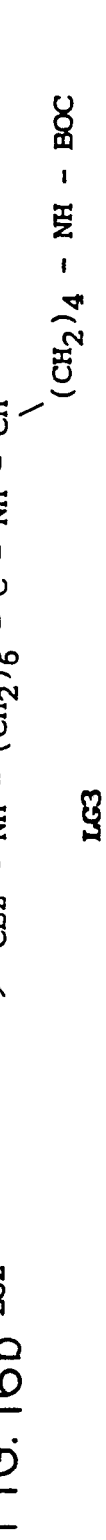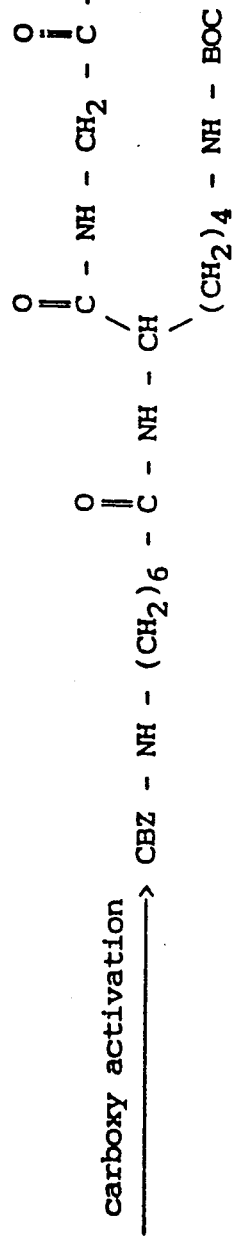
FIG. 16b  LG2 —hydrolysis→ LG3
FIG. 16c  LG3 —carboxy activation→ LG4

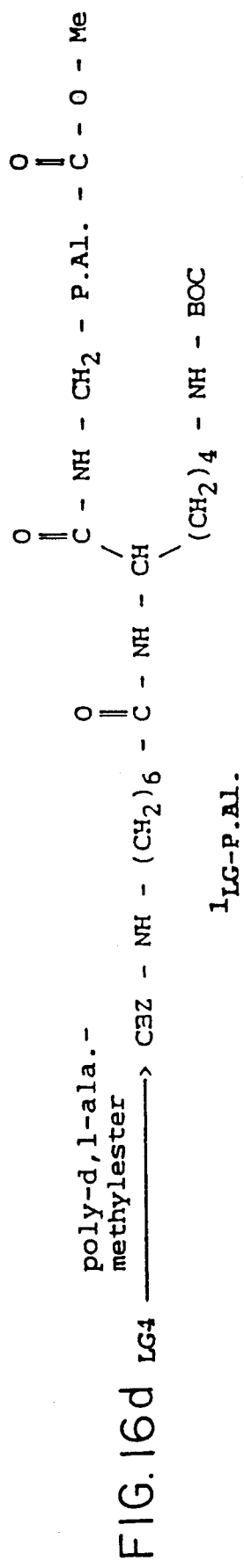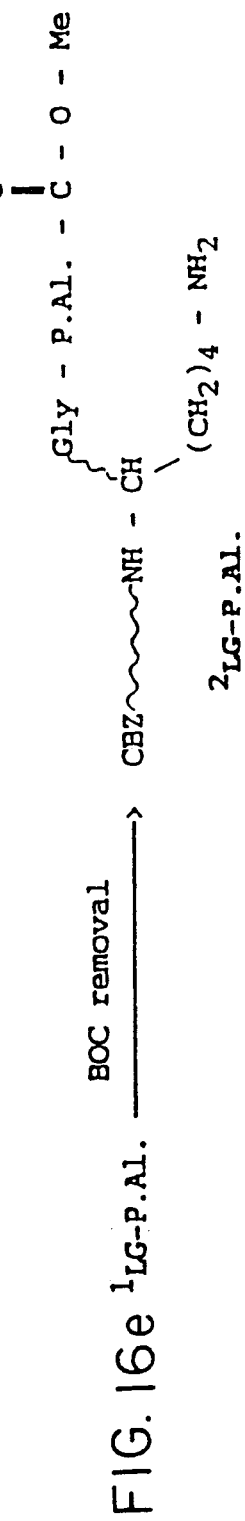
FIG.16d
FIG.16e

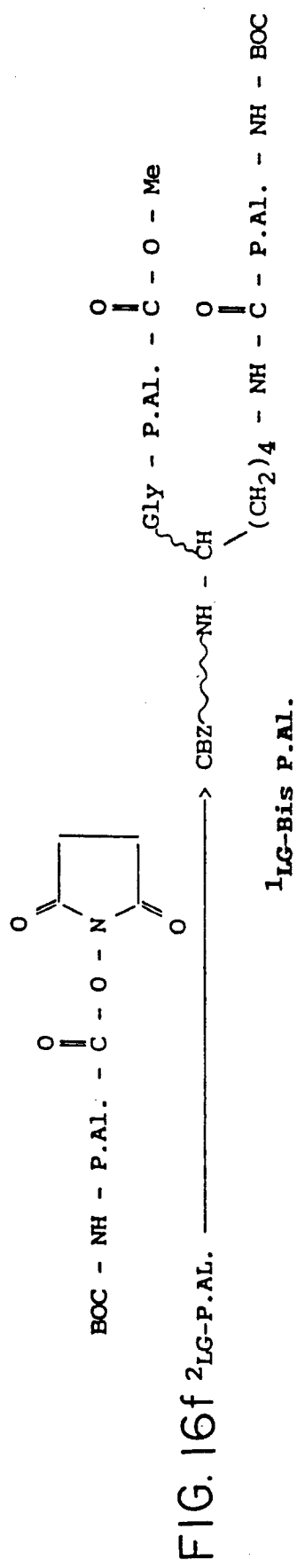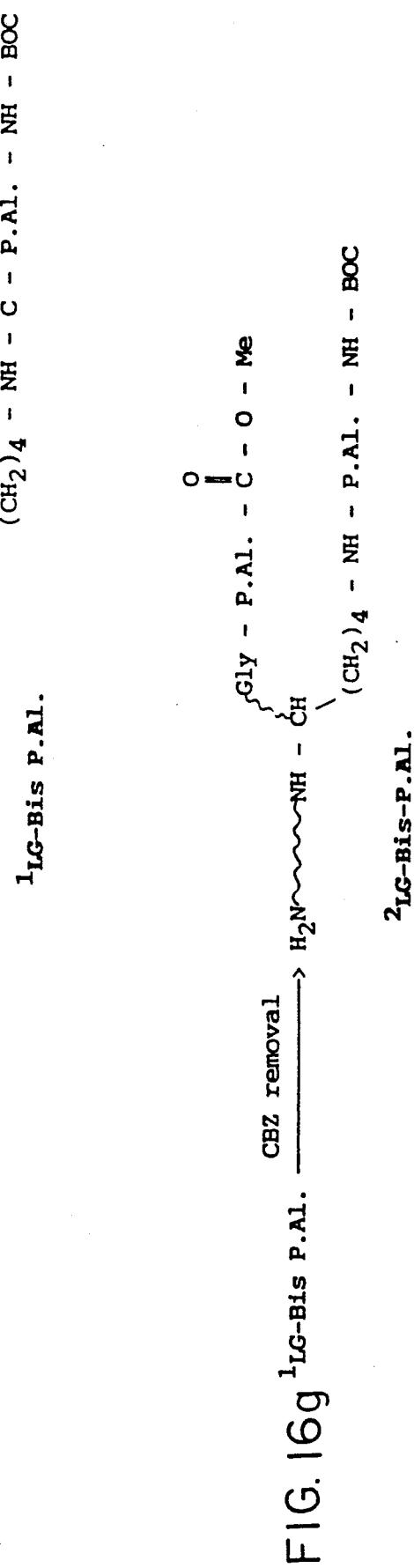

FIG. 17
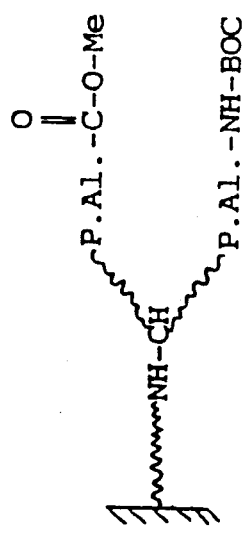
FIG. 18
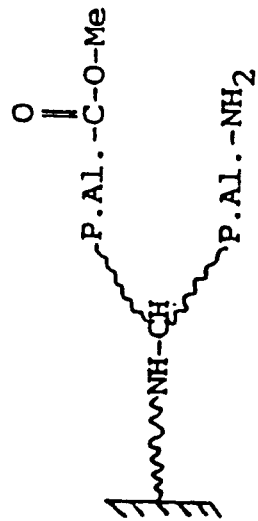
FIG. 19
Morph
Fluor.

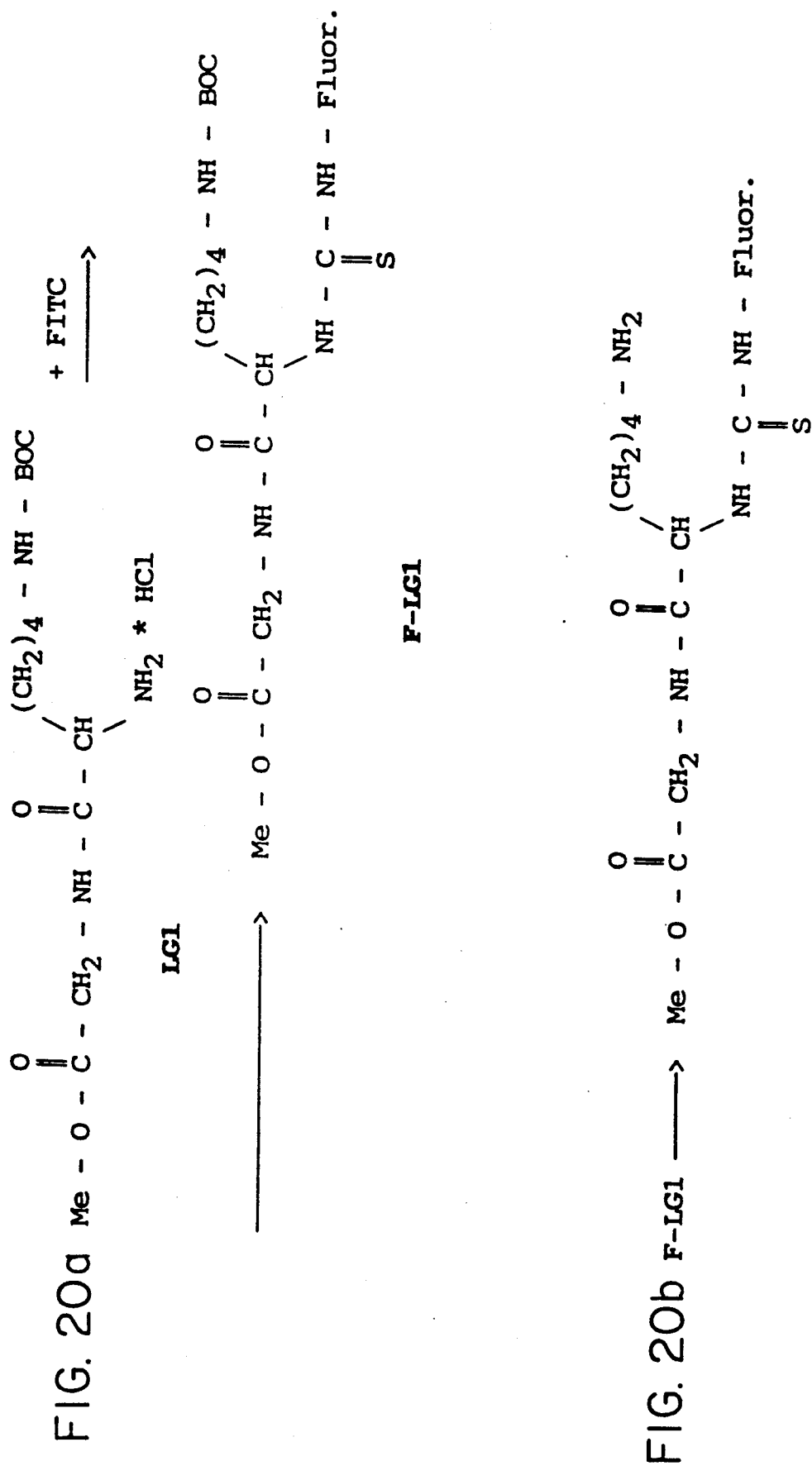

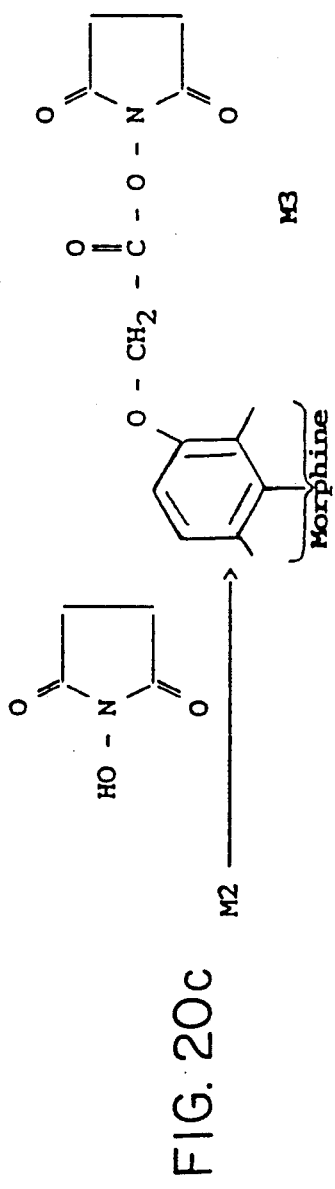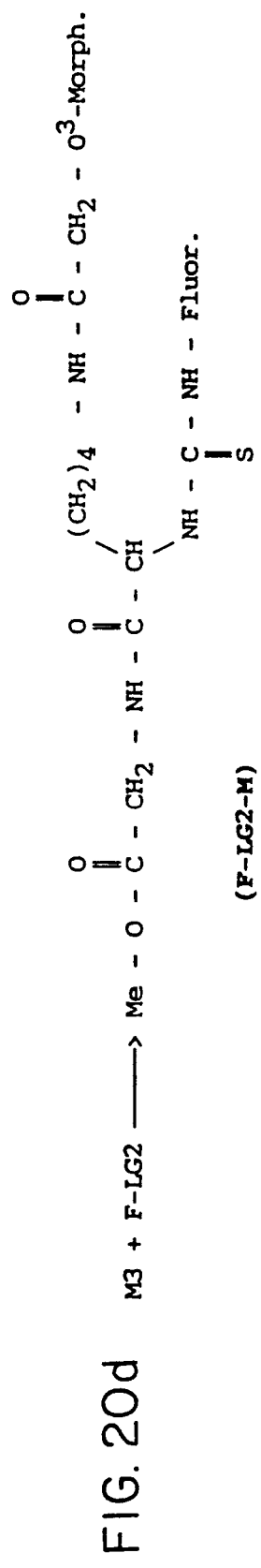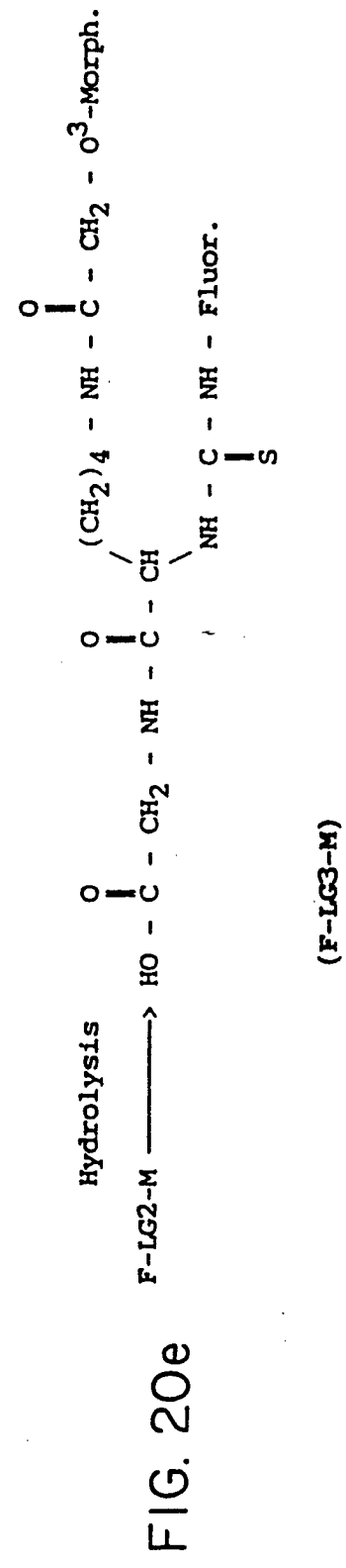
FIG. 20c
FIG. 20d
FIG. 20e

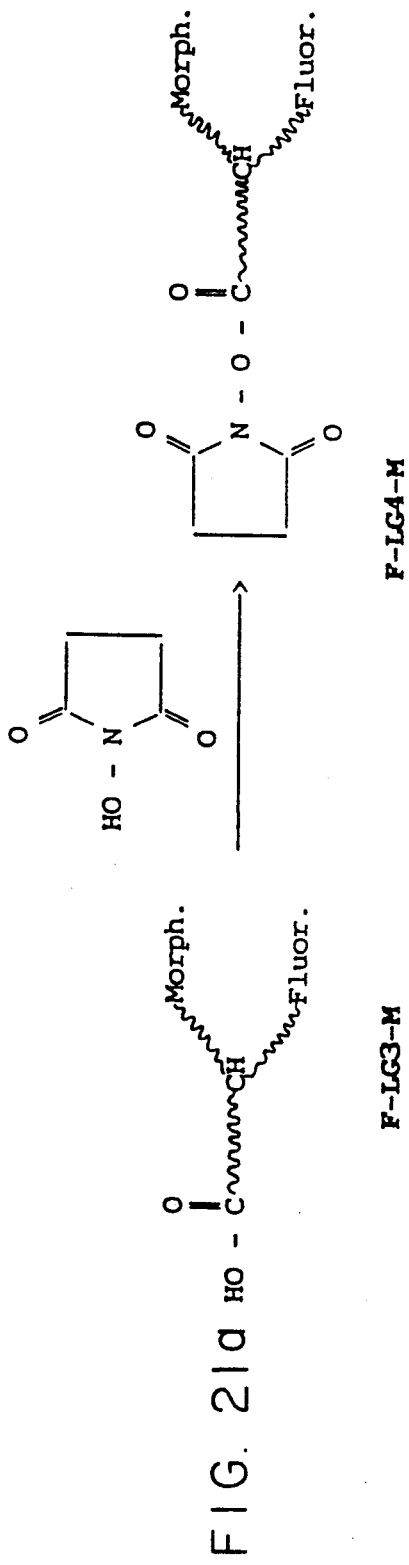
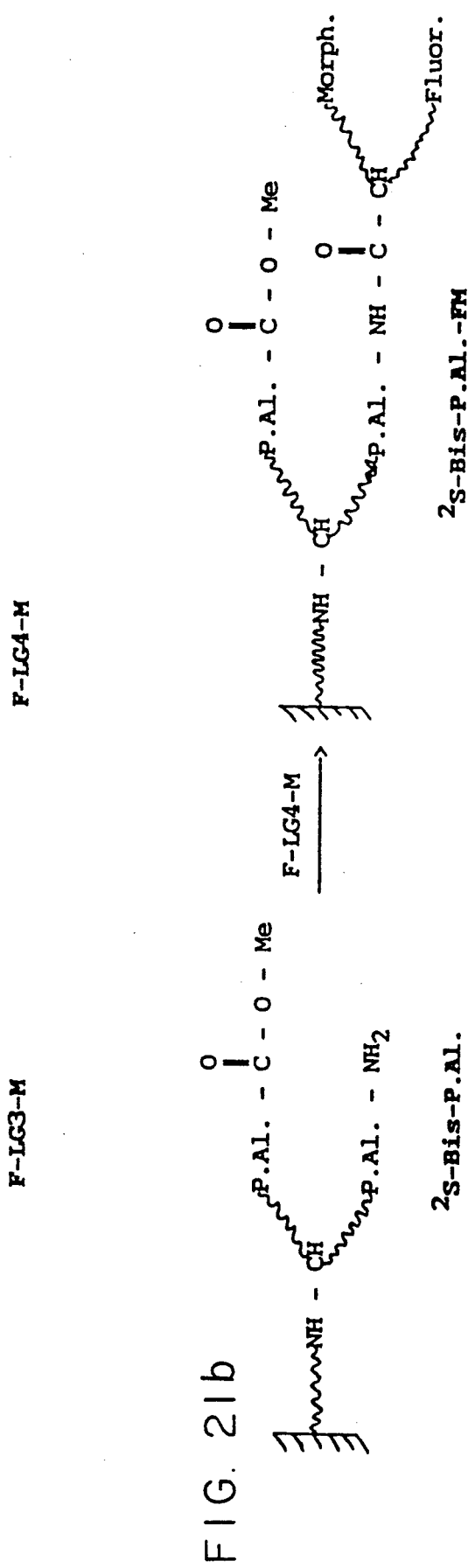
FIG. 21a
FIG. 21b

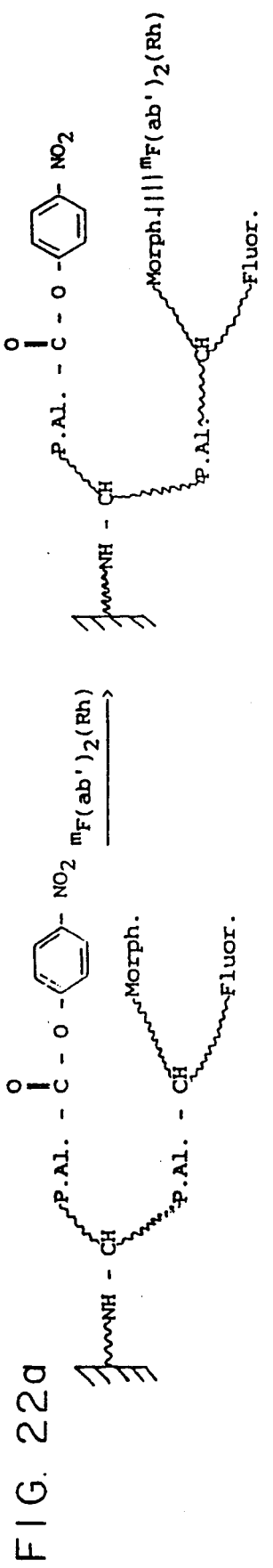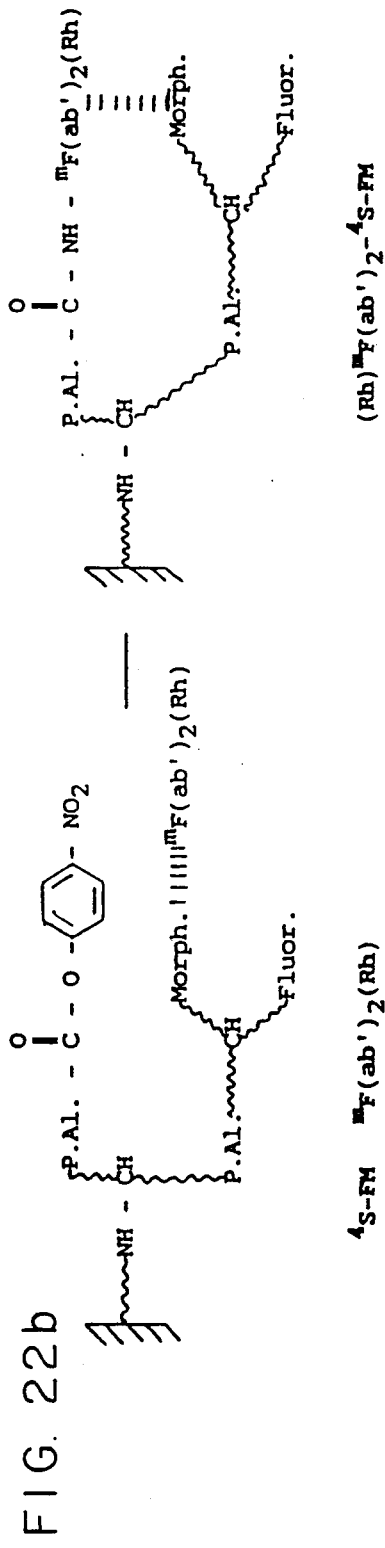
FIG. 22a
FIG. 22b

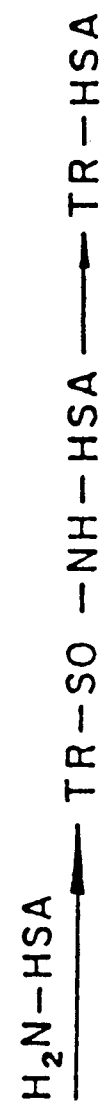
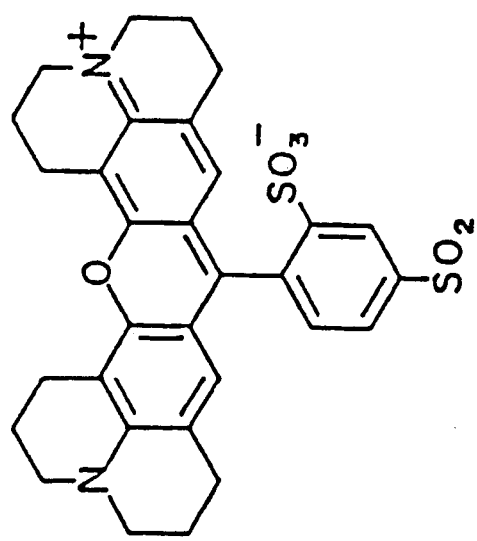
FIG. 23

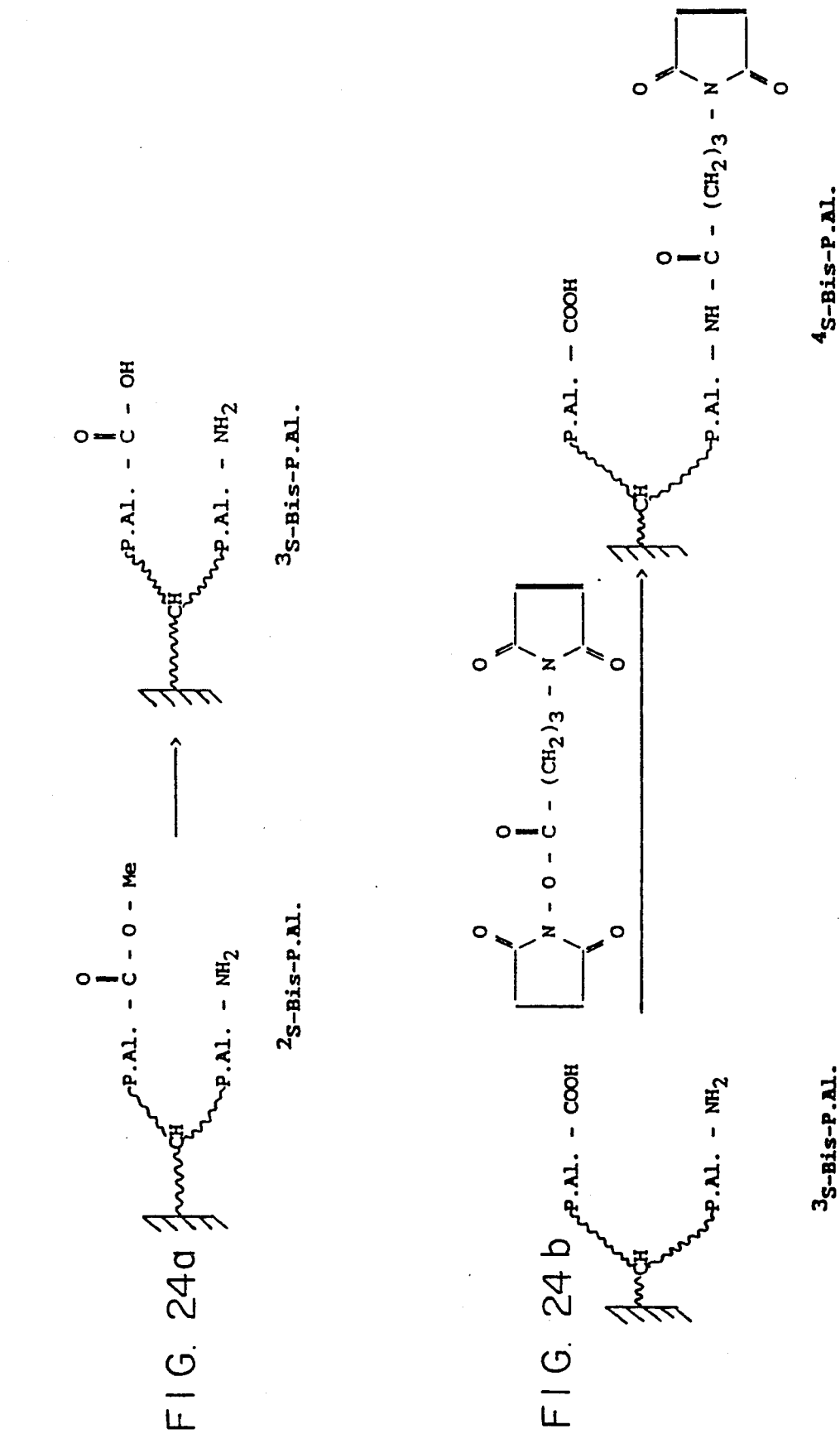

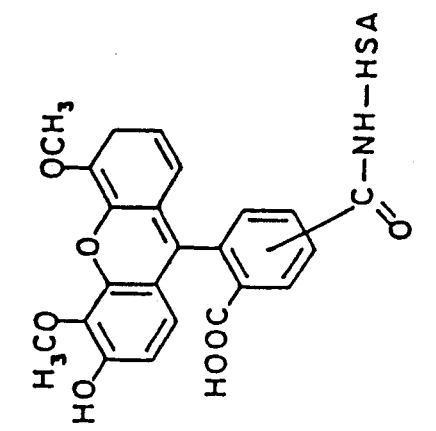
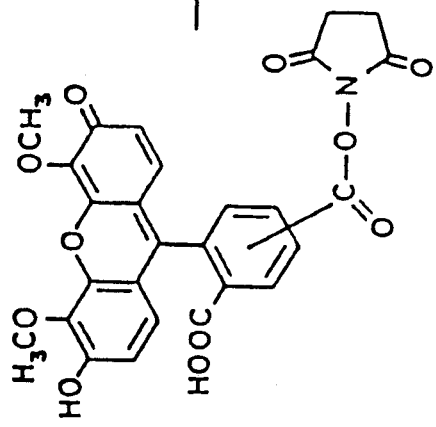
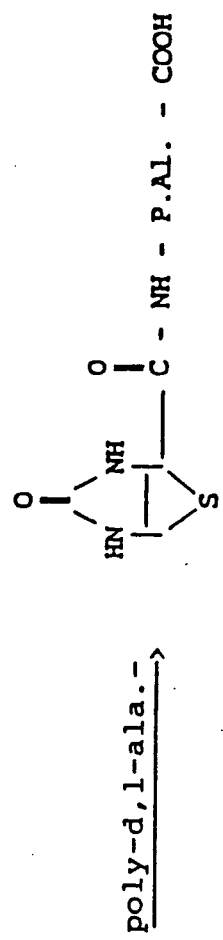
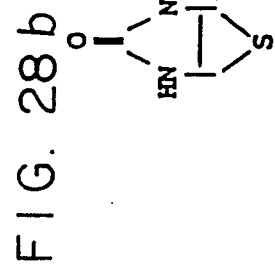
FIG. 28a
FIG. 28b

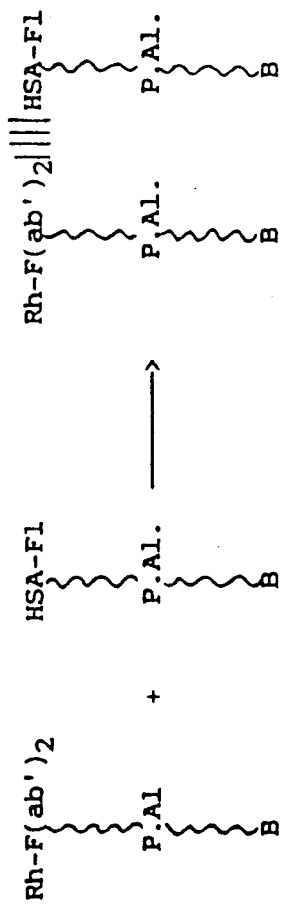
FIG. 30
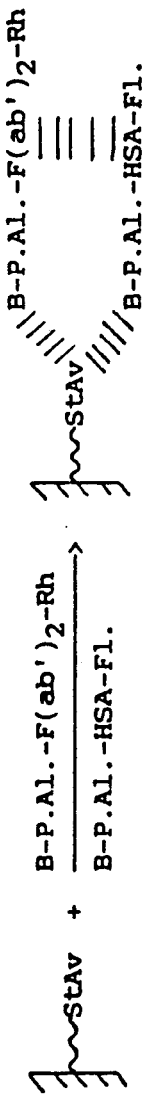
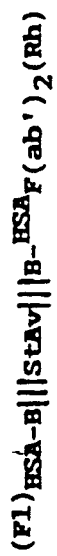
FIG. 31

ANALYTE SPECIFIC CHEMICAL SENSOR WITH A LIGAND AND AN ANALOGUE BOUND ON THE SENSING SURFACE

FIELD OF THE INVENTION

The present invention is in the field of chemical and biochemical sensors, i.e. solid-phase analytical devices that respond to the amount of a specific analyte in a tested liquid or gaseous-phase sample. The specific response to a certain analyte is obtained by an appropriate combination of a molecular recognition system for the analyte and a suitable transducer.

Biosensor is a sensor in which the recognition system is based on biological species such as the interaction between an antigen Ag, as analyte, with its antibody Ab immobilized on a sensing surface.

Chemical and biochemical sensors have a great potential for application in various fields such as medicine, industry and defence. In medicine, biosensors are useful, for example, for monitoring in vivo and in real time clinically and biochemically important analytes. Sensors for continuously monitoring analytes in real time are also of great importance in industry, e.g. for controlling and regulating chemical process, as well as in defence for monitoring biological and biochemical hazards.

LIST OF REFERENCES

1. Arnold M. A. and Meyerhoff M. E.: "Recent Advances in the Development and Analytical Applications of Biosensing Probes" Anal. Chem. 20(3) 149-196 (1988)
2. Mansouri S. and Schultz J. S.: "A Miniature Optical Glucose Sensor Based on Affinity Binding" Biotechnology Oct. 1984. 885-890.
3. Meadows D. and Schultz J. S.: "Fiber-Optic Biosensors Based on Fluorescence Energy Transfer". Talanta 35(2) 145-150 (1988).
4. Anderson F. P. and Miller W. G.: "Fiber-Optic Immunochemical Sensor for Continuous, Reversible Measurement of Phenytoin" Clin. Chem. 34(7) 1417-1421 (1988).
5. Bush D. L. and Rechnitz G. A.: "Monoclonal Antibody Biosensor for Antigen Monitoring". Anal. Lett. 20(11) 1781-1790 (1987).
6. Davis, K. A. and Leary, T. R.: "Continuous Liquid-Phase Piezoelectric Biosensors for Kinetic Immunoassays". Anal. Chem. 61 1227-1230 (1989).
7. Khanna P. L. and Ullman E. F.: "4',5'-Dimethoxy-6-carboxyfluorescein: A Novel Dipole-Dipole Coupled Fluorescence Energy Transfer Acceptor Useful for Fluorescence Immunoassays" Anal. Biochem. 108, 156-161 (1980).
8. Lim C. S., Miller J. N. and Bridges J. W.: "Energy-Transfer Immunoassay: A Study of the Experimental Parameters in an Assay for Human Serum Albumin". Anal. Biochem. 108, 176-184 (1980).
9. Bright F. V. and McGown L. B.: "Homogeneous Immunoassay of Phenobarbital by Phase-Resolved Fluorescence Spectroscopy" Talanta 32(1) 15-18 (1985).
10. Tahboub Y. R. and McGown L. B.: "Phase-Resolved Fluoroimmunoassay of Human Serum Albumin" Anal. Chim. Acta 182, 185-191 (1986).
11. Hemmila I., Malminen O., Mikola H. and Lovgren T.: "Homogeneous Time-Resolved Fluoroimmunoassay of Thyroxin in Serum" Clin. Chem. 34(11) 2320-2322 (1988).
12. Morrison L. E.: "Time-Resolved Detection of Energy Transfer: Theory and Application of Immunoassays" Anal. Chem. 174, 101-120 (1988).
13. Li T. M., Benovic J. L. and Burd J. F.: "Serum Theophylline Determination by Fluorescence Polarization Immunoassay Utilizing an Umbelliferone Derivative as a Fluorescent Label" Anal. Biochem. 118, 102-107 (1981).
14. Lowe C. R.: "The Affinity Electrode" FEBS Lett. 106(2) 405-408 (1979).
15. Sutherland R. M., Dahne C., Place J. F. and Ringrose A. R.: "Immunoassays at a Quartz-Liquid Interface: Theory, Instrumentation and Preliminary Application to the Fluorescent Immunoassay of Human Immunoglobulin G". J. Immunological Methods, 74, 253-265 (1984).
16. Andrade J. D., Vanwagenen R. A., Gregonis D. E., Newby K. and Lin J. N.: "Remote Fiber-Optic Biosensors Based on Evanescent-Excited Fluoro-Immunoassay: Concept and Progress" IEEE Transactions on Electron Devices ED-32(7) 1175-1179 (1985).
17. Axelrod, D., Burghardt, T. P. and Thompson, N. L. "Total Internal Reflection Fluorescence". Ann. Rev. Biophys. Bioeng. 13: 247-268 (1984).
18. Watkins, R. W. and Robertson, C. R.: "A total Internal Reflection Technique for the Examination of Protein Adsorption". J. Biomed. Mater. Res. 11: 915-938 (1977).
19. Ullamn, F., Schwarzberg, M. and Rubinstein, K.: "Fluorescent Excitation Transfer Immunoassay—A General Method for Determination of Antigens". J. Biol. Chem. 251: 4172-4178 (1976).
20. Tromberg, B. J. and Sepaniak, M. J.: "Fiber-Optic Chemical Sensors for Competitive Binding Fluoroimmuno assay". Anal. Chem. 59: 1226-1230 (1987).
21. Anderson, G. W., Zimmerman, J. E. and Callahan, F. M.: "The Use of Esters of N-Hydroxysuccinimide in Peptide Synthesis". J.A.C.S. 86: 1839-1842 (1964).
22. Tarbell, D. S. Yamamoto, Y. and Pope, B. M.: "New Method to Prepare N-t-Butoxycarbonyl Derivatives and the corresponding Sulfur Analogs from Di-t-Butyl Dicarbonate or Di-t-Butyl Dithiol Dicarbonates and Amino Acids". Proc. Natl. Acad. Sci. USA 69: 730-732 (1972).
23. Felix, A. M., Heimer, E. P., Lambros, T. J., Tzougraki, C. and Maienhofer, J.: "Rapid Removal of Protecting Groups from Peptides by Catalytic Transfer Hydrogenation with 1,4-Cyclohexadiene". J. Org. Chem. 43: 4194-4196 (1978).
24. McGregor, A. R., Crookall-Greening, J. O., Landon, J. and Smith, D. S.: "Polarizatin Fluoroimmunoassay of Phenytoin". Clin. Chim. Acta 83: 161-166 (1978).
25. Parini, C., Bacigalupo, M. A. Colombi, S., Ferrara, L., Franceschetti, F. and Saita, R.: "Two New Fluorescent Derivatives of Progestrone to Use in Fluoroimmunoassay". Steroids 46: 903-913 (1985).
26. Bodanszky M. and Vigneaud, V. D.: "A Method of Synthesis of Long Peptide Chains Using a Synthesis of Oxytocin as an Example" J. Amer. Chem. Soc. 81: 5688-5691 (1959).
27. Chan, M. A., Bellem, A. C. and Diamendis, E. P.: "Time-resoled Immunofluorometric Assay of Alpha-Fetoprotein in Serum and Amniotic Fluid, with a Novel Detection System." Clim. Chem. 33: 200-2003 (1987).

28. Claassen, E., Doorsma D. M., Kors N. and Van Rooijen N.: "Double-Enzyme Conjugates, Producing an Intermediate Color, for Simultaneous and Direct Detection of Three Different Intracellular Immunogloblin Determinants With Only Two Enzymes." J. Histochem. Cytochem. 34: 423-428 (1986).

29. Bhatia, S. K., Shriver-Lake, L. C., Prior, K. J., Georger, J. H., Calvert, J. M., Bredehorst, R. and Ligler, F. S.: "Use of Thiol- Terminal Silanes and Heterobifunctional Cross-linkers for Immobilization of Antibodies on Silica surfaces". Anal. Biochem. 178: 408-413 (1989).

30. Bayer, E. A. and Wilchek, M.: "The Use of the Avidin-Biotin Complex as a Tool in Molecular Biology". Methods in Biochem. Analysis 26: 1-45 (1980).

BACKGROUND OF THE INVENTION AND PRIOR ART

Interest in chemical and biochemical sensors has expanded rapidly in recent years. One of the more recent developments has been the attempt to develop immunosensors based on optical fibres, which are usually characterized by their high specificity and high sensitivity. These and other developments focused on an attempt to adapt the principles of solid-phase immunoassay to continuous monitoring of various substances e.g. drugs, hormones etc. in body fluids. Immunosensors developed for these purposes are usually based on the conventional competitive immunoassay reaction between an immobilized receptor present in a solid phase on the one hand and a mobile ligand (analyte) and a mobile labelled analogue of the latter present in a liquid phase on the other hand. Such a reaction may be described by the following equation:

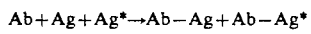

$$Ab + Ag + Ag^* \rightarrow Ab-Ag + Ab-Ag^*$$

In this equation Ab is the receptor and stands for an antibody and Ag and Ag* are the ligands and stand for an antigen analyte and a labelled derivative of the same antigen or of an analogue thereof, respectively.

According to the elementary immunoassay method for the determination of an analyte Ag in a test liquid, a sample of the tested liquid containing a known amount of labelled antigen Ag* and an unknown amount of the analyte Ag is introduced into a vessel holding a solid phase containing a given amount of an appropriate antibody Ab. Upon contact, the analyte antigen Ag present in the sample and the added labelled antigen Ag* compete for the limited amount of antibody Ab in the solid phase. After a certain incubation period the liquid and the solid phases are separated from each other, the solid phase is washed and the analyte concentration is determined by following the labelled component, either as Ag* in the liquid phase or as the conjugate Ab—Ag* in the solid phase.

In known solid-phase immunoassays only one component of the competitive recognition system (usually the antibody Ab) is immobilized on the sensing area, while the labelled antigen Ag* is introduced ad hoc into the liquid sample which is tested for the antigen Ag.

The above-described immunoassay method is static and unsuitable for the continuous determination of analyte in real or nearly real time. A further development in the field of immunoassay was achieved by the employment of probes which enable discrete measurements of analytes, although not in real time. In one version of these probes the sensing tip, with predetermined amounts of immobilized receptors, is dipped in a test liquid containing a known amount of labelled ligand and unknown amount of analyte ligand. From the relative amount of the labelled ligand which conjugated to the receptors, present on the sensing tip, the concentration of the analyte is determined. By a sequence of such discrete measurements the change in concentration of the analyte with time may be determined in close approximation.

In sensors in which a labelled antigen or a labelled receptor (one of them is an analogue to the analyte) is used, the concentration of the labelled species has to be kept constant in order to serve as a reliable reference for the continuously changing concentration of the analyte. Subject to this it is further required that the receptor-ligand affinity interaction be specific and reversible so that the system will responds continuously and reversably to changes of analyte concentration.

Various approaches have been proposed to solve the latter problem. Some of these proposals are based on a compromise in that a degree of reversibility is obtained by so selecting the receptor that the affinity between receptors and ligands is moderated. However, by its very nature such a compromise solution is not quite satisfactory as the sensing is less specific and it is liable to yield false results. Consequently, efforts are continuously made to find better solutions for the desired reversibility while keeping high specificity of the competitive recognition system.

Recently, some approaches, based mainly on encapsulated reagents, have been proposed (Refs. 1-5). Thus, for example, Mansouri and Schultz (Ref. 2) have developed an optical affinity glucose sensor, in which a labelled glucose analogue in the form of high molecular weight fluoresceindextran is entrapped within a dialysis fibre having an outer membrane permeable to glucose. A given amount of concanavalin-A is covalently attached to the inner lumen of the dialysis fibre, and the entrapped fluoresceinated dextran and permeating glucose compete for conjugation therewith. At equilibrium the level of free fluorescein in the hollow fibre lumen is measured via the optical fibre and is correlated to the concentration of glucose. The higher the glucose concentration, the higher the recorded fluorescence.

Similar biosensors have been proposed by Meadows and Schultz (Ref. 3) and by Anderson and Miller (Ref. 4). In these systems, which are based on fluorescence energy transfer, the specific receptor and the high molecular weight labelled ligand are enclosed within a dialysis membrane, permeable to the low molecular weight unlabelled ligand such as glucose or phenytoin.

A further system, based on potentiometric response, has been proposed by Bush and Rechnitz (Ref. 5). A monoclonal antibody Ab is trapped between two membranes while its antigen (DNP) is immobilized on one of the membranes.

In all the known biosensor systems according to Reference 1 to 5, one or more of the competitive reagents is enclosed within a membrane permeable to the low molecular weight analyte molecules, but not permeable to their labelled analogues. This is essential in order to meet the requirement for a constant level of labelled analyte analogues within the sensing zone. The result is that all these biosensing systems are suitable only for low molecular weight analytes.

A further disadvantage of the above prior art sensors is that since the analyte has to diffuse through the membrane, the response time is increased.

Recently, Davis and Leary (1989), Ref. 6, have developed a piezoelectric device for kinetic immunoassay which is based on the change of crystal frequency as a function of analyte concentration. Although the authors refer to this as a biosensor, within the definitions herein this piezoelectric device is a probe and not a sensor. Thus, although Davis's system does not require the use of a labelled antigen and consequently no semipermable membrane, and although it measures continuously for a certain time, it is not reversible. Accordingly, in this piezoelectrical system, whenever a new sample has to be measured the chemical sensing tip has to be restored to activity by washing at pH 3 at which the conjugates are dissociated.

It is an object of the present invention to provide a new concept for chemical and biochemical sensors which combines effectively the features of stability, specificity and reversibility without restriction on the size of the analyte.

Another object of the invention is to provide a sensor which does not need a semipermeable membrane while still keeping a constant predetermined amount of analogue receptors or analogue ligands (labelled or unlabelled) in the sensing area. This type of sensor is more suitable for in-vivo applications.

The new concept is also applicable to a probe as well as for immunoassay without the need to add extra reagents, for example an analog-analyte as normally used in the conventional immunoassays.

GLOSSARY

The following are the meanings of some of the terms used in the description and claims herein:

Species—molecules, radicals, cells and ions;

Receptor—any species capable of conjugating with specific ligands via affinity interaction;

Ligand—any species capable of conjugating specifically with a receptor via affinity interaction;

Reversible Competitive Recognition Unit (RCRU)—A unit which is composed of at least two constituent components, namely at least one receptor and at least one ligand (labelled or unlabelled) wherein one of them is an analogue of the analyte and the other is a specific recognizer of the analyte.

Competitive Recognition System—A system comprising as constituent components receptors and ligands whose concentrations are constant;

Analyte—a ligand or a receptor whose concentration in the sample has to be determined.

Analyte Analogue—A constituent component of the RCRU which is a labelled or unlabelled ligand or receptor whose specific affinity interaction with the recognizer is the same as or similar to that between the recognizer and the analyte.

Recognizer—A constituent component of RCRU which is a receptor or ligand whose specific affinity interaction with the analyte is the same as or similar to that with the analyte analogue.

Affinity bond—a non-covalent bond between two species;

RL-Conjugate—an association between a receptor and a ligand held together by an affinity bond;

Chemical sensor—any type of solid phase recognition system bearing immobilized receptors and ligands, operating by the reversible formation of RL-conjugates, regardless of the chemical nature of any of the recognizer, analyte analogue and analyte;

Sensing surface—a portion of a chemical sensor that bears Reversible Competitive Recognition Units;

GENERAL DESCRIPTION OF THE INVENTION

In the following the invention will occasionally be specifically described with reference to immunosensors, it being understood that the invention is in no way confined thereto and covers quite generally chemical sensors within the meaning of this term as defined hereinabove.

From the foregoing description of the background of the invention it follows that in prior art chemical sensors the components of the competitive chemical recognition systems (the receptor and the analogue ligand) are completely separated from each other when the receptor is conjugated with the analyte ligands. Also in the prior art sensor systems, only one component of the competitive recognition system (the receptor or the ligand) is immobilized on the sensor while the other, although entrapped within a space enclosed by a semipermeable membrane, is relatively mobile in the liquid phase within that space that contains the analyte.

The present invention is based on an entirely new concept. According to this concept, the sensing surface is coated with reversible competitive recognition units (RCRUs) each of which contains as constituent components at least one receptor and at least one ligand, one of which components is an analyte analogue. In these RCRUs the receptor and the ligand are a priori connected to each other, directly or indirectly, in such configuration that even when, for example, an analyte analogue ligand is displaced from the receptor by an analyte ligand, the analogue will still be retained in relatively close proximity to the receptor. In addition, the relative positions of the receptor and the ligand in the RCRU are such that when no analytes are present or when the analyte concentration is at a low level, they are affinity conjugated by a specific affinity interaction.

According to the present invention, the RCRU which is immobilized on the sensing surface, is the basic chemical sensing unit which enables the real time continuous and reversible monitoring of the analyte in a tested sample. As will be explained below, the unique features of the RCRU are gained as a result of its unique structure and configuration.

The invention provides an analyte specific chemical sensor for determining an analyte in a test medium, comprising a carrier body with a sensing surface having attached thereto a plurality of RCRUs each comprising as constituent components at least one receptor and one ligand arranged in such relationship that in the absence of analyte the receptor(s) and ligand(s) of each RCRU associate to form an inner conjugate which conjugate is capable of dissociating in the presence of the analyte and reassociating when the analyte concentration in the test medium is low.

If desired the constituent receptor(s) and ligand(s), of each RCRU, are bound directly to the sensing surface (hereinafter "direct linkage"). Preferably, however, the binding is indirect, via spacer molecules which are interposed between each of the constituent components and the sensing surface (hereinafter "indirect linkage").

In accordance with one embodiment of the indirect linkage each of the receptor(s) and ligand(s) of each RCRU are bound via a separate spacer molecule.

In accordance with other embodiments the constituent components of the RCRU are interconnected, either by a common spacer molecule or directly, in case the species are large enough, to form a molecular construct with the receptor and the ligand moieties, which construct is linked to the sensing surface, either directly or by means of a further spacer molecule.

In the indirect linkage configuration of the RCRUs of chemical sensors according to the invention it is possible by judicious selection of the spacer molecules based on general common knowledge of the chemical and stereo-chemical properties of the RCRU-receptors, the RCRU-ligands and spacer molecules, to optimize the distance between the receptor and the ligand thereby to ensure a stable yet reversible affinity bond between the constituent components in an RCRU.

The new concept underlying the present invention is of a universal character and applies to various specific receptors, for example receptors of hormones, vitamins, neurotransmitters, toxins etc. Also it is applicable to other receptor-ligand systems such as antibody-antigen; glycoconjugation-lectins; metal interacting macromolecules-metal ions; etc.

The new chemical sensors according to the invention can be applied for the determination of a great variety of different types of analytes, e.g. low molecular weight compounds such as drugs and hormones; high molecular weight compounds such as proteins, enzymes, DNA and RNA molecules; cells; and many more in either liquid or gaseous test samples. The preferred configuration of a sensor according to the invention to be used for a particular case is determined with due regard to the various parameters of the analyte under consideration.

The fluctuations of analyte concentrations in the tested sample affect the chemical occurrences at the RCRUs, and consequently the physico-chemical characteristics of the components thereof. The changes in the analyte concentration are monitored, according to the present invention, by continuously measuring the changes of the above physico-chemical characteristics induced by occurrences at the RCRUs, namely the inner association and dissociation thereof. Such physico-chemical characteristics may be, for example, photochemical, e.g. light absorption, light emission, light scattering and light polarization; electrochemical; and piezoelectrical.

Hence, a chemical sensor according to the invention functions as a transducer that converts chemical occurrences at the RCRUs into detectable physical phenomena, e.g. by producing an optical, electrochemical or piezoelectrical response. If desired, the carrier body may form part of the transducing system.

According to one embodiment of the present invention there is provided a chemical sensor as defined herein, wherein each RCRU comprises an electrochemical group, which reacts upon association and/or dissociation of an RL-conjugate, to produce an electric signal. In such embodiments the carrier body may be an electrode or a field effect transistor (FET).

In sensors with luminophore labelled analyte analogues, e.g. ligands, the luminescence characteristics are under certain excitation conditions correlated to the concentration of the analyte in the tested sample. This is the preferred mode of detection in accordance with the invention.

Generally, the physical characteristics of light which is emitted by a labelled analyte analogue is different in the conjugated and the non-conjugated states. Accordingly the changes in the concentration of analyte may be monitored by observing the alterations of the luminescent emission.

One way of causing and detecting luminescence in a sensor according to the invention, is to design the carrier body as a waveguide so that the evanescent light wave propagating at the solid phase/liquid or gaseus phase interface excites the luminophore analyte analogue and the emitted luminiscence is conducted via the waveguide to an appropriate detector.

If desired the distinction between the inner conjugated and non-conjugated states of the RCRU components may be sharpened by fitting each recognizer, e.g. receptor, of the RCRUs with a luminescence quencher group while the analogue analyte, e.g. ligand, contains a luminophore group. In this way luminescence in the state of inner conjugation between the receptors and labelled ligands of an RCRUs which occurs in the absence of analyte, is eliminated or minimized due to the energy transfer between the luminophore group of the labelled ligand and the quencher group of the receptor. When the fluorophore labelled ligand is displaced from the conjugate by a competing analyte, the energy transfer between the group of the labelled ligand and the quencher group of the receptor is minimized, and as a result the luminescence increases. Similarly, each recognizer may be fitted with a luminescence enhancer, and in such a case, the luminescence increases upon formation of the R-L conjugate and decreases upon dissaciation of the conjugate.

Where the physicochemical characteristic of the RCRU is piezoelectrical, the carrier body is a crystal whose frequency is modulated by fluctuations of analyte in the test medium.

Due to the reversible nature of the RCRUs of a sensor according to the invention, there is a real time response to fluctuations of analyte concentrations in the test medium with concomitant continuous modulations of the intensity of the detected phenomena which are recorded by suitable detection instrumentation, for example of the kind described by Sutherland et al. (Ref. 15), Tromberg et al. (Ref. 20), and Bush and Rechnitz (Ref. 5).

The invention also provides an apparatus for measuring the concentration of an analyte either in liquid or gaseous phase, comprising a probing vessel fitted with a sensor of the kind specified herein and transducing means which transduce the receptor-ligand interactions into a measurable physico-chemical phenomenon. If desired, such apparatus may be designed as monitor for continuous operation with said probing vessel being adapted for the continuous throughflow of liquid or gaseous test fluid.

In accordance with a further aspect of the present invention there is provided a method for preparing a chemical sensor of the kind specified, which method comprises interacting the constituent components of an RCRUs of the kind specified herein, to form at least one affinity bond between them, and then attaching the RCRUs directly or indirectly to the carrier body by covalent bonds and/or affinity bonds.

In accordance with a modification of this method one of the constituent components of each RCRU is first attached to the carrier body and is then interacted with the remaining constituent components of the RCRUs by covalent or affinity interactions to yield a conjugate and thereafter the said remaining constituent components are attached to the carrier body.

DESCRIPTION OF THE DRAWINGS

For better understanding the invention will now be described, by way of example only, with reference to the annexed drawings to which it is not limited. In the drawings:

FIGS. 8i–10v show different reaction schemes for the formation of immobilized RCRUs on a sensing surface of a sensor according to the invention;

FIGS. 15 to 31 are various formulae and reaction schemes relating to matters described in the Examples herein.

DESCRIPTION OF SPECIFIC EMBODIMENTS

Figure 1:
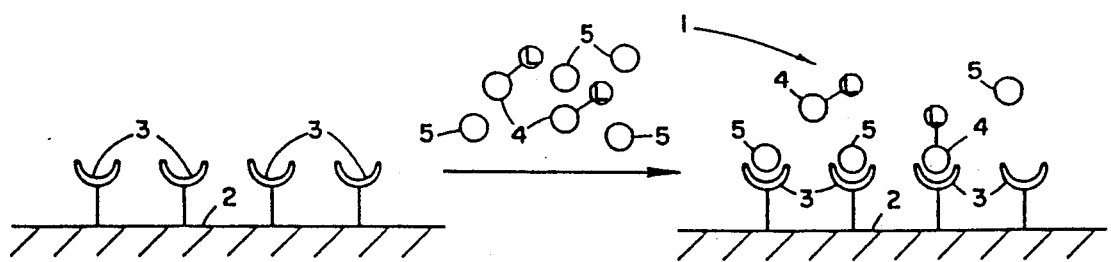
FIG. 1 is a conceptual illustration of the functioning of a prior art solid phase competitive immunoprobe.

FIG. 1 is a conceptual illustration of the functioning of a prior art solid phase immunoprobe in which the receptors serve as recognizers and are immobilized on the sensing surface of the probe body, while the labelled ligands, which serve as analyte analogues, are dispersed, together with the analyte, in the liquid sample to be tested. As shown, a probe 1 has a sensing surface 2 to which are covalently bonded receptors 3. The labelled ligands 4 are dispersed in the tested liquid sample together with the analytes 5 and in the course of testing the labelled ligands 4 and analytes 5 compete for free receptors 3 as shown on the right-hand side of FIG. 1. Each labelled ligand 4 has a labelling group L. At the end of the analysis the solid phase is separated from the liquid phase, washed and the concentration of the analyte 5 in the solution is computed from the determination of the amount of labelling groups L on the probe.

Attention is now directed to FIG. 2 which illustrates conceptually six different embodiments of RCRUs in sensors according to the invention. The conceptual illustrations are with reference to immuno-sensors, it being understood that the invention is not confined thereto. In FIG. 2 Ab designates an antibody which in this case is the receptor, Ag* designates an antigen analogue which is the RCRU-ligand. Full lines represent covalent bonds and dashed lines represent affinity bonds.

Figure 2A:
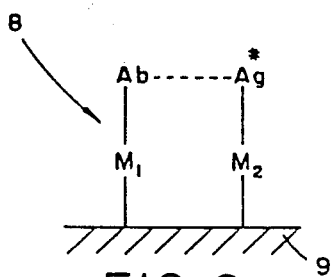
FIG. 2a–2f shows conceptually six different embodiments of RCRU of a chemical sensor according to the invention.

FIG. 2(a) shows the simplest form of a RCRU according to the invention. As shown the RCRU 8 is anchored on the sensing surface 9 of a carrier body (not shown). It comprises one Ab and one Ag* molecule linked each separately to the sensing surface 9 by means of spacer molecules M1 and M2, respectively, which may be the same or different. The bonds between each of Ab and Ag* and the associated spacer molecule M1 and M2 and between these latter and the sensing surface 9 are all covalent. It is further seen that normally, when no analyte is present, Ab and Ag* of each RCRUs are associated by an affinity bond to form an Ab—Ag* conjugate.

Figure 2B:
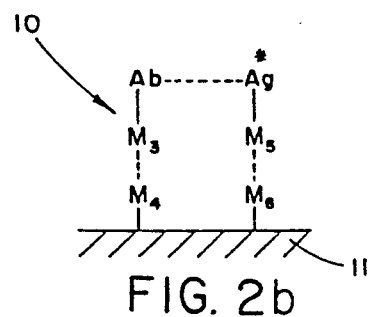

The RCRU 10 of FIG. 2(b) is similar but in this case each of Ab and Ag* is associated with two spacer molecules M3 and M4 and M5 and M6, respectively, with the bonds between M3 and M4 and between M5 and M6 being affinity bonds while those between Ab and M3, Ag* and M5 and each of M4 and M6 and the sensing surface 11 being covalent. Conceptually the RCRUs of FIGS. 2(a) and 2(b) are similar.

Figure 2C:
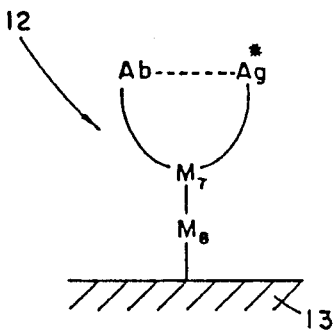

In the embodiment of FIG. 2(c) Ab and Ag* (of the RCRU 12) are linked to the two opposite ends of a spacer molecule M7 which in turn is linked via another spacer molecule M8 to the sensing surface 13. All bonds which lead from Ab and Ag* to sensing surface 13 are covalent.

Figure 2D:
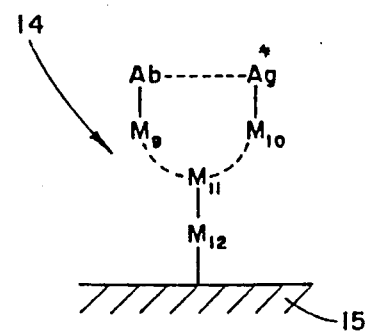

In accordance with the embodiment of FIG. 2(d), Ab and Ag* (of the RCRU 14) are linked covalently to spacer molecules M9 and M10 respectively, the latter are linked by affinity bonds to another spacer molecule M11 which in turn is linked covalently to yet another spacer molecule M12 which in turn is linked covalently to the sensing surface 15. Conceptually this RCRUs is similar to that of FIG. 2(c).

Figure 2E:
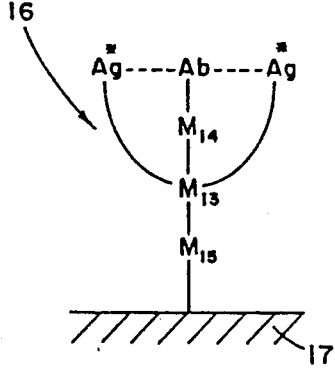

In accordance with FIG. 2(e), the RCRU 16 contains two Ag* species which are associated with one Ab which is positioned between them. The two Ag* species are linked to the two ends of a spacer molecule M13 to which Ab is also linked via another spacer molecule M14. M13 is linked to a further spacer molecule M15 which in turn is linked to the sensing surface 17. All bonds which lead from the two Ag* species and the Ab to the sensing surface 17 are covalent.

Figure 2F:
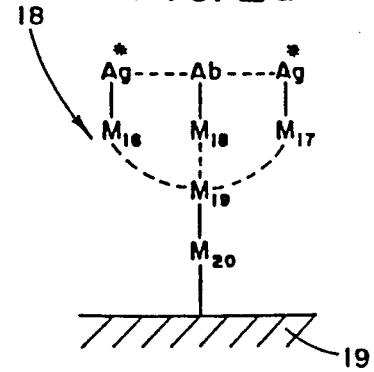

The RCRU 18, of the embodiment described in FIG. 2(f) also contains two Ag* species associated with one Ab. The two Ag* species and Ab are linked covalently to spacer molecules M16, M17 and M18 respectively, all of which are linked via affinity bonds to another spacer molecule M19 which in turn is bonded covalently to a spacer molecule M20, the latter being covalently bonded to the sensing surface 19. In accordance with the embodiments of FIG. 2(c) to FIG. 2(f), an affinity reversible interaction occurs also between a receptor of one RCRU and an analog ligand of a neighbouring RCRU.

In all the embodiments of FIG. 2(a) to 2(f) the various spacer molecules M are so selected that the distance between each Ab and an associated Ag* is optimized so as to enable formation of a specific affinity bond between the Ab and the Ag* of the RCRU, in the absence or in relatively low concentration of analyte species. In addition, when this specific inter RCRU conjugate dissociates, for example under competitive interactions of the analyte antigens, the displaced RCRU-antigen, although being still connected to the receptor (by the spacer molecules) behaves as if it were free in the solution.

As it has been already mentioned, the chemical components of the RCRU may contain labelled or unlabelled groups. An example of applying a sensor, according to the present invention, without using a label group is the case when the sensing is based on a piezoelectrical effect. In this case the sensing will be more suitable for analytes of the higher molecular weights.

Figure 3A:
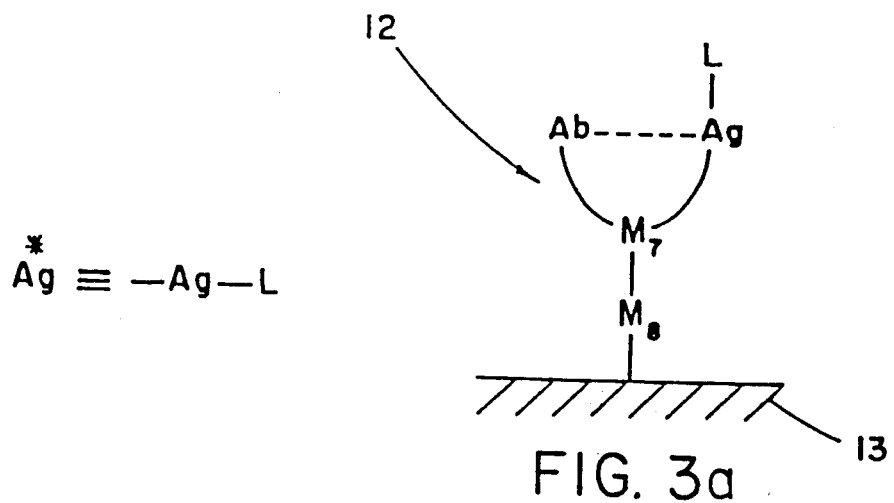
FIG. 3a–3c shows conceptually several forms of linkage of a labelled ligand in the RCRU.
Figure 3B:
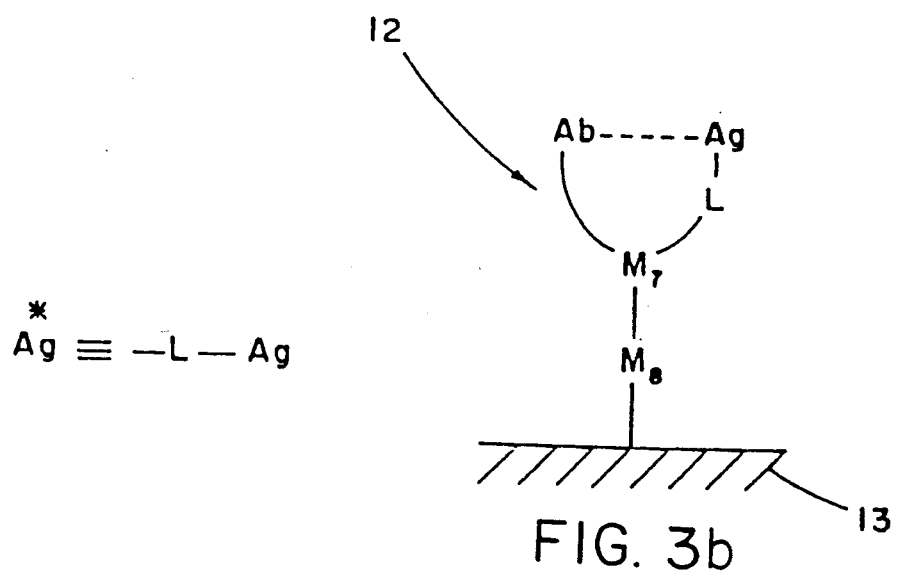
Figure 3C:
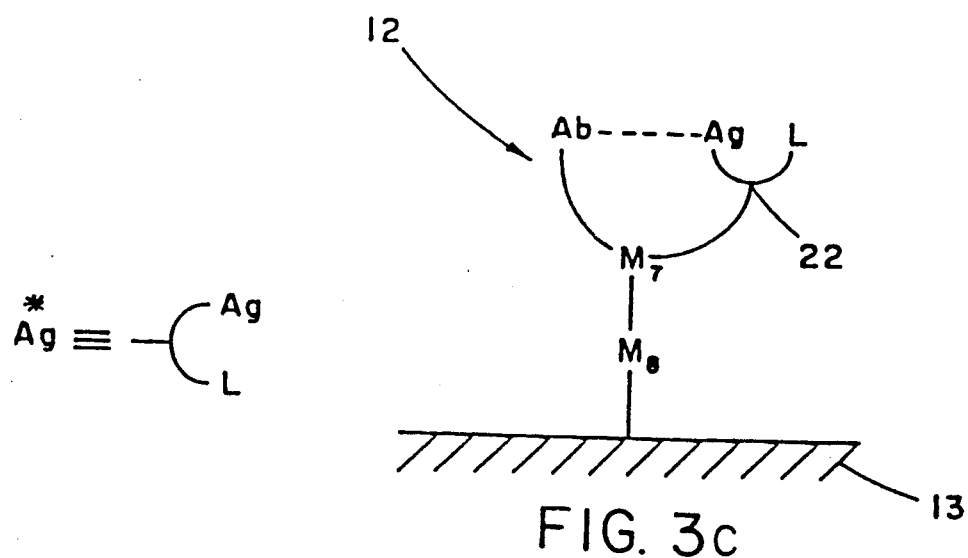

When Ag* contains a label group, L, it can be fitted into a RCRU in various ways as shown in FIG. 3. In that Figure three different modifications are shown with reference to the RCRU embodiment of FIG. 2(c) and the same reference signs are used. In all of FIGS. 3(a), 3(b) and 3(c), Ag* of FIG. 2(c) is replaced by Ag-L which in FIG. 3(a) is -Ag-L, in FIG. 3(b) is -L-Ag and in FIG. 3(c) is

Accordingly, in FIG. 3(a) L is linked to M7 via Ag, in FIG. 3(b) Ag is linked to M7 via L and in FIG. 3(c) Ag and L are linked in parallel to a juncture 22 which is linked to M7. Which of these modifications will be used in practice will depend on the nature of the analytes and labelling. Assuming L to be a fluorophore group, the embodiment of FIG. 3(a) will, as a rule, be used for high molecular weight antigens and/or small labelling groups while those of FIG. 3(b) will as a rule, be preferred when Ag is of low molecular weight and L is a high molecular weight fluorophore such as phycobiliprotein.

The embodiment of FIG. 3(c) is suitable in cases where L and Ag are of low molecular weight.

FIGS. 4 to 7 illustrate conceptually the functioning of sensors according to the invention having RCRUs of the kind illustrated conceptually in FIGS. 3(a), 3(b) and 3(c), respectively. In these drawings all spacer molecules are for the sake of simplicity of illustration shown by way of drawn-out lines. Thus in FIG. 4, the configuration of the RCRUs 23 which are immobilized on the sensing surface 24, is in accordance with FIG. 3a. With no analyte Ag or a very low concentration thereof in the liquid phase the equilibrium is shifted to internal conjugation with each Ab in a RCRU conjugating with the associated Ag-L. When the concentration of the analyte Ag in the tested sample increases the equilibrium is shifted to the right with the result shown on the right-hand side of FIG. 4. As seen in that state some of the Ab/Ag-L affinity bonds are severed and the labelled antigens Ag-L are displaced by analytes Ag. With a decrease of the concentration of the analyte Ag the equilibrium again shifts to the left; and so forth. When groups L are, for example, fluorophore they are of such a nature that there is a significant difference between their light emission in the conjugated and non-conjugated state and the ensuing fluorescent light modulations are recorded by a suitable recorder.

Figure 5:
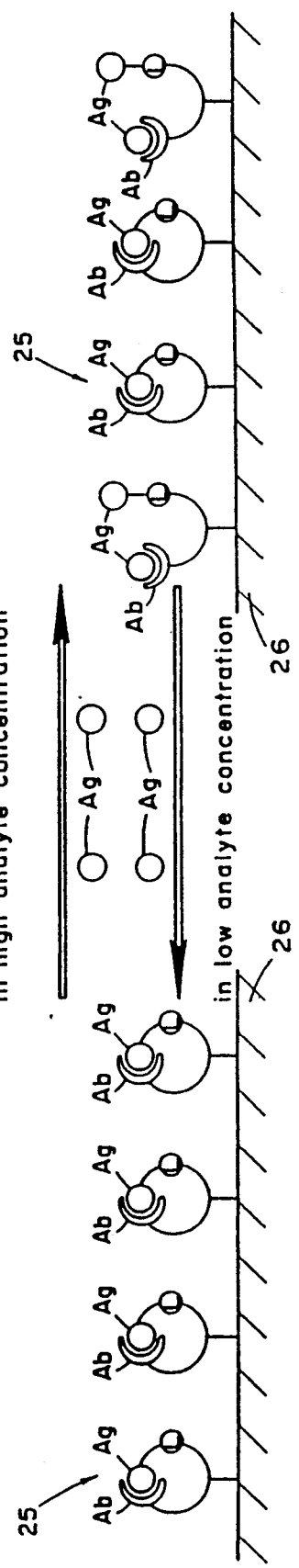

FIG. 5 is a similar conceptual representation with the configuration of the RCRUs 25, which are immobilized on the sensing surface 26 being in accordance with FIG. 3(b). Likewise FIG. 6 is a similar conceptual representation with the configuration of the RCRUs 27, immobilized on a sensing surface 28, being in accordance with FIG. 3(c).

Figure 4:
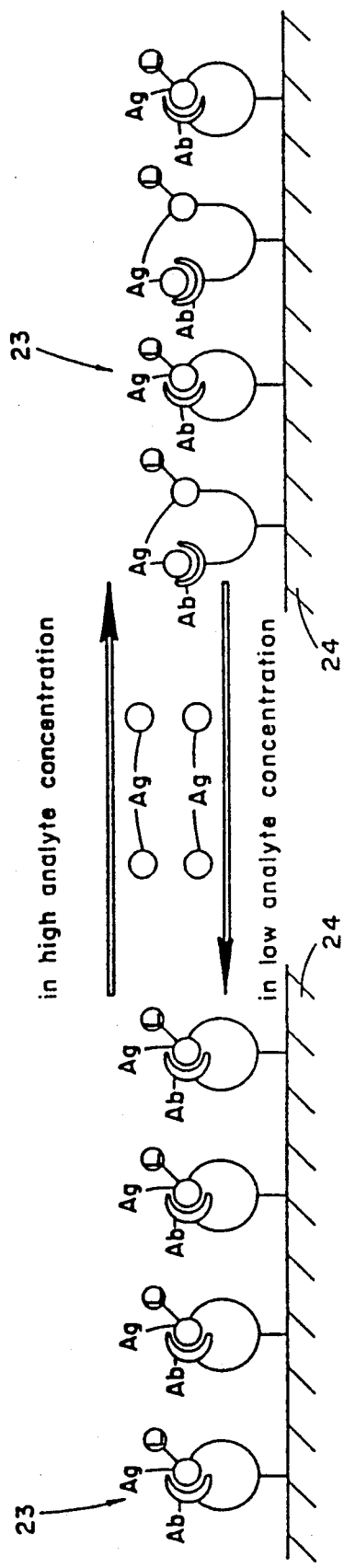
FIGS. 4–7 are conceptual representations of the functioning of different chemical sensors according to the invention.
Figure 6:
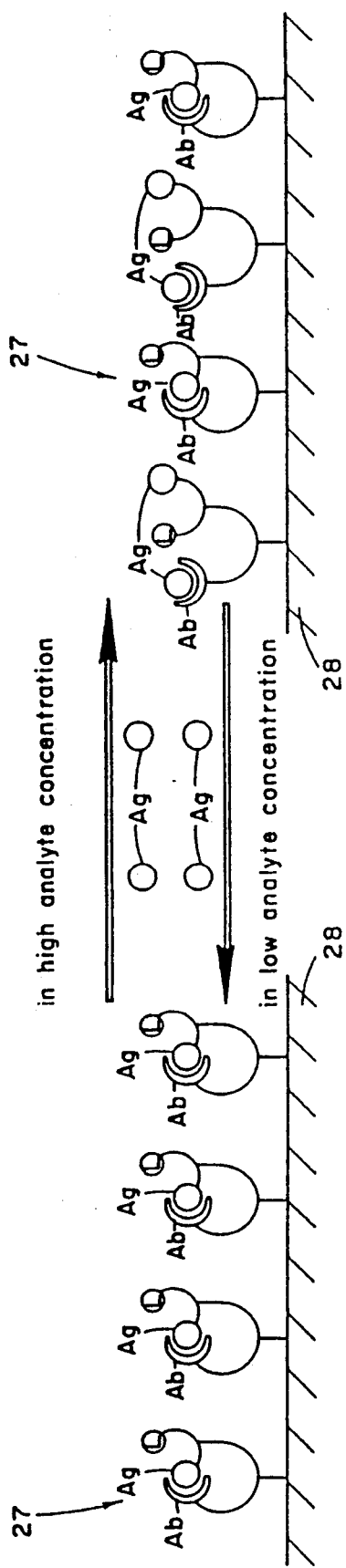
Figure 7:
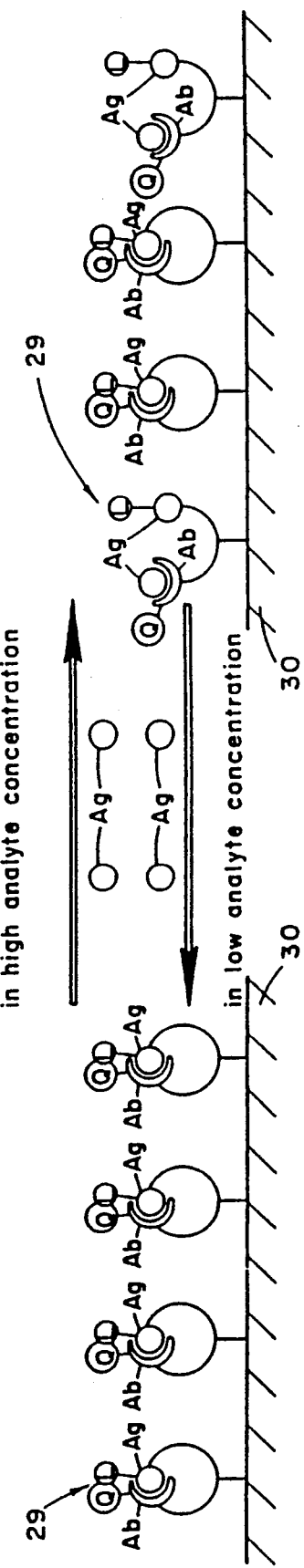

In the conceptual representation of FIG. 7 in which the manner of presentation is similar to that in FIGS. 4 to 6 each Ab comprises a quenching group Q which in the inner conjugation state shown on the left-hand side of the Figure is in close affinity to the luminofluorophore group L of the associated labelled antigen analogue Ag-L, and in consequence the luminescence of the group L is quenched. When the equilibrium is shifted to the right due to the presence of the analyte Ag some of the luminescent groups L are set free with the intensity of the ensuing luminescence being proportional to the concentration of the analyte Ag in the tested sample.

FIGS. 8 to 10 show conceptually some manners of preparation of an immunosensor according to the invention with immobilized RCRUs according to FIG. 2(a). Similar as in FIG. 2 continuous lines signify covalent bonds and dashed lines affinity bonds.

Referring first to FIG. 8, it is seen that in a first step each of Ab and Ag* is reacted with a bifunctional spacer molecule M1 and M2 to yield Ab-M1 and Ag*-M2, respectively. In a second step Ab-M1 and Ag*-M2 are conjugated and in a third step the resulting conjugate is immobilized on the sensing surface of the sensor by reaction of a terminal functional group of each of M1 and M2 with suitable complementary functional group on the sensing surface.

FIG. 9 illustrates conceptually the preparation of an immunosensor according to the invention with immobilized RCRUs having the configuration of FIG. 2(c). As shown, in a first step two polyalanine molecules with terminal functional groups X and Y are bound jointly to a spacer molecule M anchored in the sensing surface. In a second step Ag* is reacted with the polyalanine-X molecule to yield a polyalanine-Ag* construct which in a third step is conjugated with a receptor antibody Ab. In a fourth step the resulting product is subjected to conditions at which Ab reacts with the neighbouring polyalanine-Y. grouping to yield the final RCRUs. Other variations are also possible. Thus, for example, steps 2-4 may be performed first and groups X and Y are then bound to the spacer molecule M.

FIG. 10 illustrates conceptually the preparation of an immuno-sensor according to the invention in which the immobilized sensing groups have the configuration of FIG. 2(d). As shown in a first step, streptavidin is linked to the sensing surface by reaction with a pre-activated hydroxyl group thereof. Independently Ag* is reacted with a compound MB where M is a spacer molecule and B is biotin, to produce Ag*-M-B. Similarly and again independently, Ab is reacted with MB to produce Ab-M-B. In a fourth step Ag*-M-B and Ab-M-B are admixed under conditions inducive of the formation of an affinity bond between Ag* and Ab and the resulting product is reacted with the immobilized streptavidin group to yield a RCRUs having the configuration of FIG. 2(d).

As will be readily understood by those versed in the art, reactants other than those specifically mentioned by way of example with reference to FIGS. 9 and 10 may be used. Furthermore, by similar approaches RCRUs of different configurations may be produced.

Figure 11:
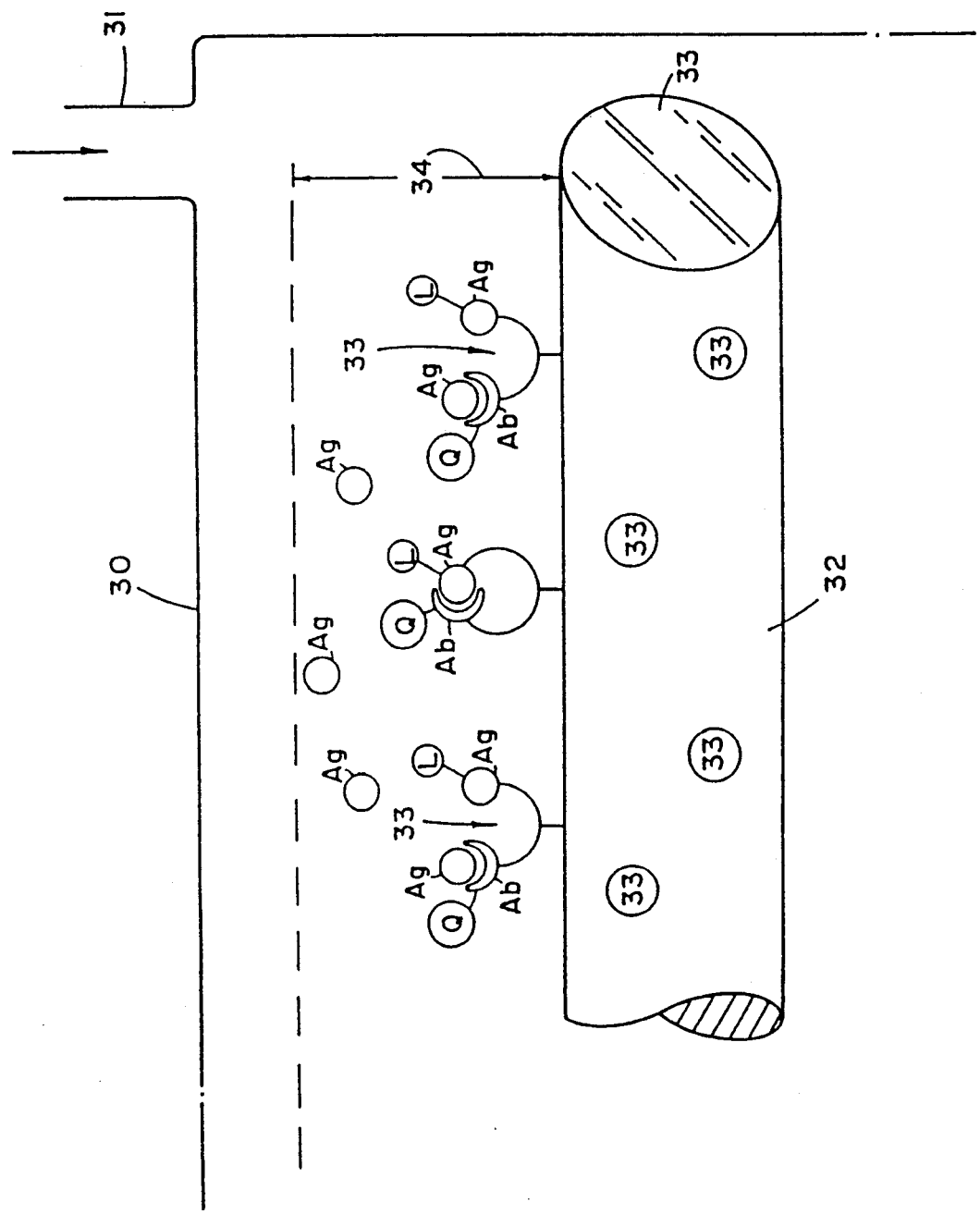
FIG. 11 is a diagrammatic illustration of a sensor according to the invention in which the carrier body is an optical fibre.

FIG. 11 shows diagrammatically a fraction of a cuvette 30 forming part of an analyzer apparatus and having an opening 31 for the ingress of a test fluid, and another opening (not shown) for the egress thereof. Mounted within the cuvette 30 is an optical fibre 32 having its free end covered by a mirror 33 while the other end is associated with a light source (not shown). On the sensing surface of the optical fibre 32 there are anchored a plurality of RCRUs 33 comprising each a receptor antibody molecule Ab bearing a quenching group Q and a labelled ligand consisting of the analyte-type antigen molecule Ag bearing a luminous fluorophore group L. In operation, light travels forth and back within the optical fibre 32 producing an evanescent light wave in zone 34. This evanescence excites the L groups present on the labelled antigen. Due to the presence of quencher groups Q on the labelled antibody, the measured intensity of the emitted fluorescence is correlated to the relative proportions of the conjugated and unconjugated labelled antigens. The higher the relative proportion of the Q-Ab Ag-L conjugate, the lower the intensity of the emitted fluorescence.

Figure 12:
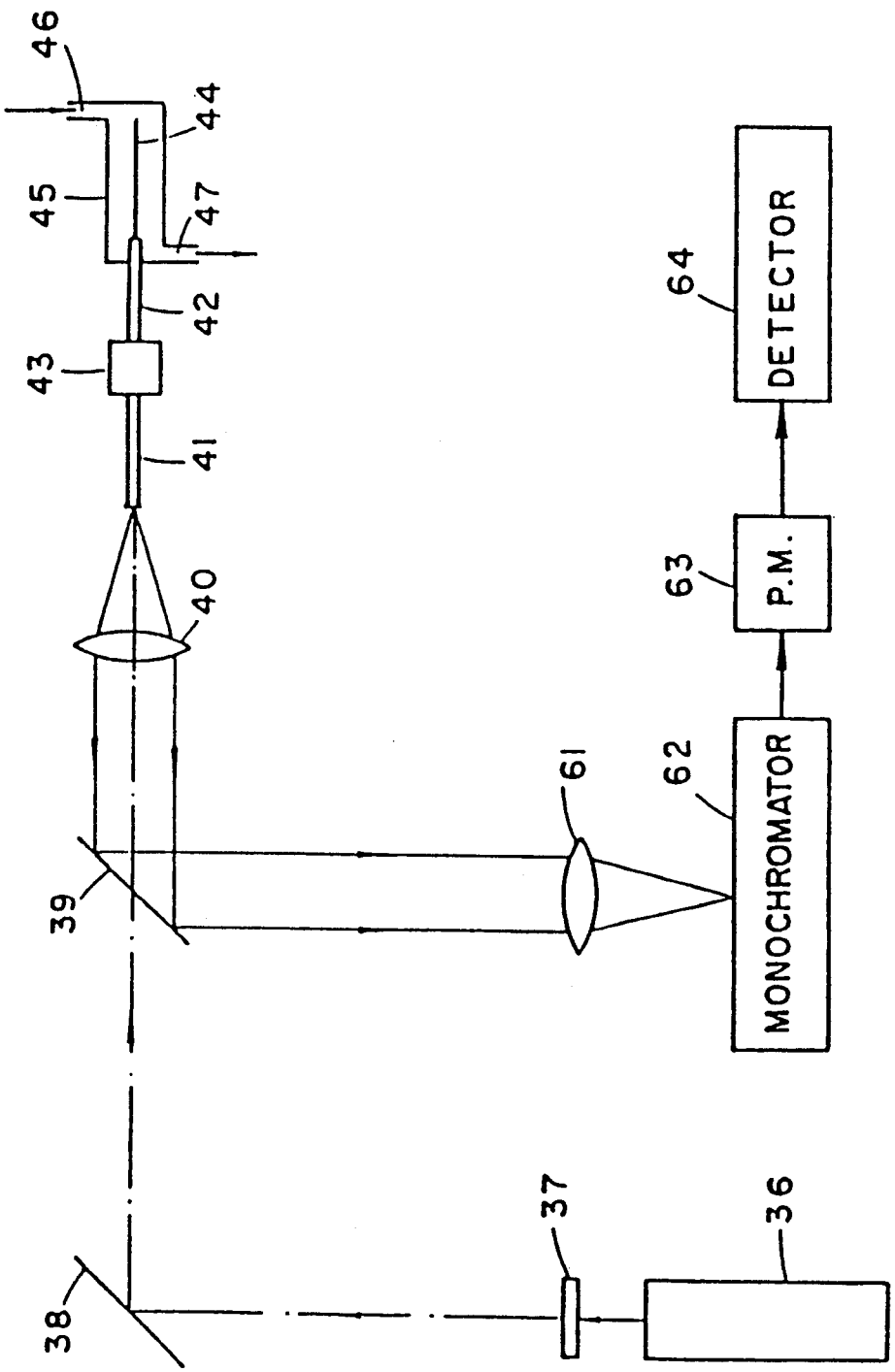
FIG. 12 is a diagrammatic illustration of a monitor embodying a sensor according to the invention.
Figure 13:
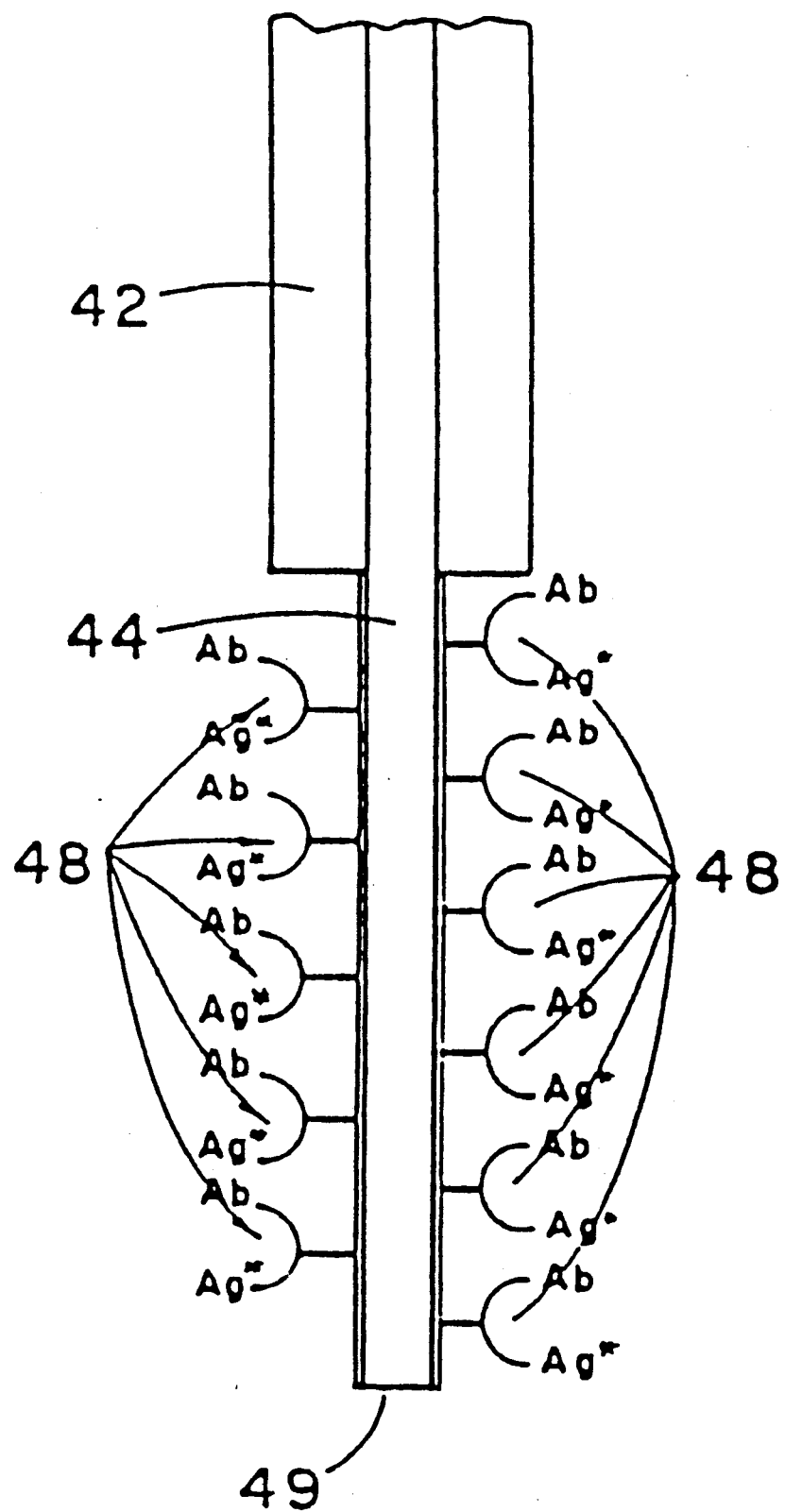
FIG. 13 is a diagrammatic illustration of the sensor used in the monitor of FIG. 12, drawn to a larger scale.

FIGS. 12 and 13 illustrate diagrammatically an apparatus for continuously monitoring the presence of an analyte Ag in a fluid and embodying an immunosensor according to the invention in which the carrier body is an optical fibre. As shown, the instrument comprises a laser light source 36 with associated laser line filter 37, a first mirror 38 and a second, dichroic mirror 39 which is transparent to the laser light and reflects fluorescent light. A condensing lens 40 focuses the incoming laser light into a first optical fibre 41 which is coupled to the sensor 42 by means of a fibre coupler 43. The waveguide 42 comprises an unclad sensing portion 44 which is located within a cuvette 45 having an inlet 46 and outlet 47 for the ingress and egress, respectively, of the test fluid. The evanescence produced within cuvette 45 around the sensing portion 44 of sensor 42 at the solid phase/fluid interface excites the luminous groups of RCRUs 48 which may, for example, have the configuration shown in FIG. 7.

The role of mirror 49 is to double the path of light propagating inside the fibre and thus to amplify the optical signal. The resulting omnidirectional fluorescence is conducted via lens 40, mirror 39 and a further lens 61 into a monochromator 62 and from there via a photomultiplier 63 to a detector 64. The latter comprises a microprocessor and a printer to produce a tracing showing the modulation of the fluorescence with time. If desired, the detected light modulations may be computed into concentration fluctuations of Ag so that the printout will show directly the latter.

Figure 14:
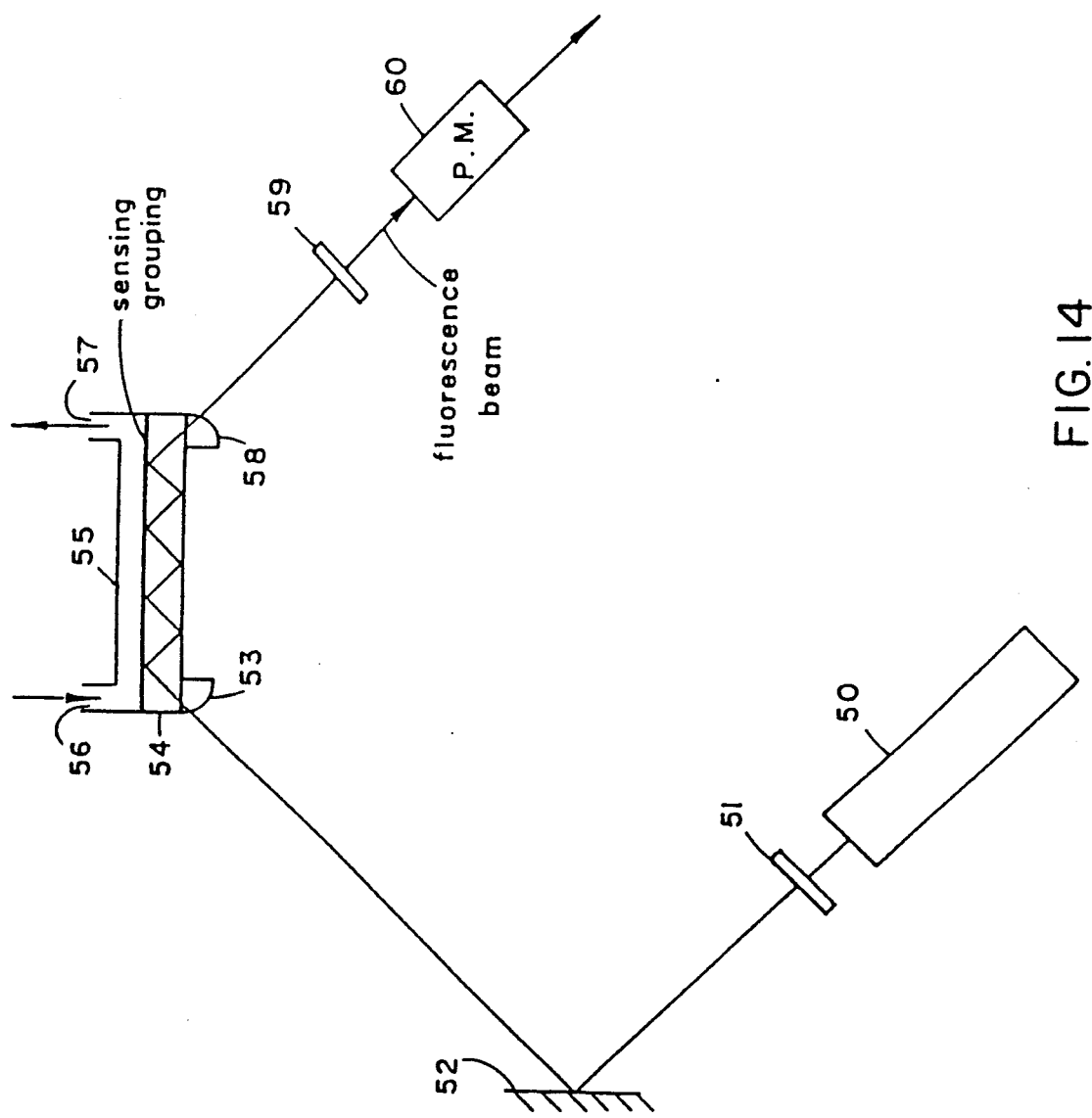
FIG. 14 is a diagrammatic illustration of another type of monitor embodying a sensor according to the invention.

Another embodiment of a device embodying an immunosensor according to the invention is shown in FIG. 14. Laser light is produced by a generator 50 associated with a laser light filter 51 and is reflected by means of mirror 52 and conducted via a prism 53 into an immunosensor according to the invention 54, comprising a waveguide slide whose upper face constitutes the sensing surface and comprises a solid phase coat with a plurality of RCRUs anchored therein. The slide waveguide 54 is enclosed within a cuvette 55 with inlet 56 and outlet 57 for ingress and egress, respectively of the tested sample. At the edge opposite to that at which the light enters, the slide waveguide 54 is associated with another prism 58 which directs the fluorescent beam resulting from the excitation of luminous groups of the RCRUs by the laser beam, to a filter 59 and from there via a photomultiplier unit 60 to further processing and recording as known per se. The laser light coming out of the waveguide 54 is directed away by prism 58 so as not to impinge on the pulse moderator beam.

EXAMPLES

The examples below are provided to illustrate, but in no way to limit the present invention. The following are the meanings of the abbreviations and symbols in the examples:

ABBREVIATIONS

Ab: antibody
Ab*: labelled or analogue antibody
Ag: antigen
Ag*: labelled or analogue antigen
BOC: t-butoxy carbonyl ($C_4H_9OCO-$)
B: biotin
CBZ: benzyloxycarbonyl ($C_6H_5CH_2OCO-$)
DCC: dicyclohexylcarbodiimide ($C_6H_{11}N=C=NC_6H_{11}$)
DMF: N,N-dimethylformamide
F: fluorophore
FITC: fluoresceinisothiocyanate
$^mF(ab')_2$: $F(ab')_2$ fragment for morphine
$^{HSA}F(ab')_2$: $F(ab')_2$ fragment for HSA
GMBS: N- -maleimidebutyryloxy succinimide ester
HSA: human serum albumin
CIU: competitive immuno unit
L: label species
LG1: N-$\epsilon$-BOC-lysylglycine-t-butylester*HCl
MDS: mercaptomethyl-dimethylethoxysilane
M2: $O^3$-carboxymethyl morphine
NHS: N-hydroxysuccinimide
PBS: phosphate buffered saline
P.Al: poly-d,l-alanine
Q: quencher
R1: $N^7$-CBZ-heptanoic-succinimidylester
RCIU: reversible competitive immuno unit
RCRU: reversible competitive recognition unit
Rh2: tetramethylrhodamine-5-isothiocyanate
StAv: streptavidin
TR: texas red

SYMBOLS

| | |
|---|---|
| ---- | single covalent bond |
| ∼∼∼ | spacer group (connected covalently) |
| ‖‖‖‖ | specific affinity interaction |
| ▨▨▨ | sensing surface |

EXAMPLE 1

Figures 15, 16A:
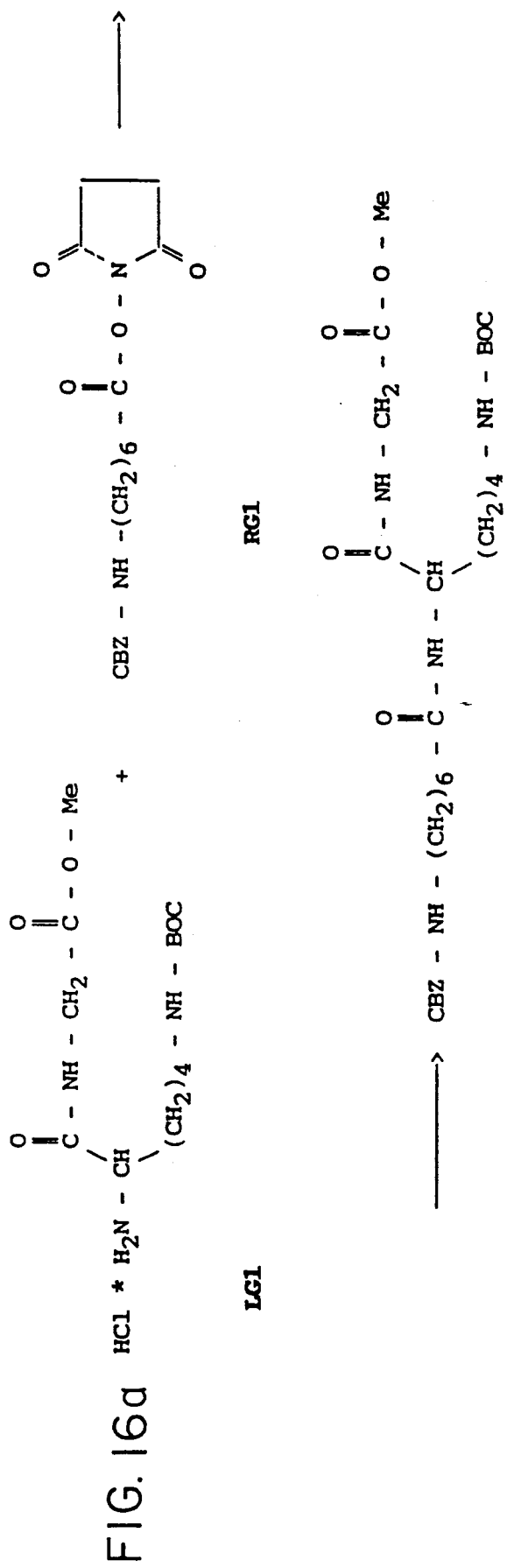

Preparation of immobilized bis-polyalanine on the sensing surface (fused silica) for immunosensor of the type illustrated in FIG. 2(c). Specifically, the RCRAs have the configuration of FIG. 15.

STRATEGY 1.1—Preparation of the bis-polyalanine)
1.2—Activation of the silica surface)
1.3—Immobilization of the bis-polyalanine on the silica surface)

1.1 Preparation of the bis-polyalanine ($^2$LG-Bis-P.Al.)

This preparation includes several steps, using conventional procedures, described in the literature) The preparation process is depicted in the scheme of FIG. 16.

a) Product LG2: N-$\epsilon$-BOC-lysylglycine methylester-hydrochloride (LG1) is reacted with $N^7$-CBZ-heptanoicsuccineimidyl ester (R1) under similar conditions used by Anderson et al (1964), (21), to obtain the product LG2.

b) Product LG3: Saponification of LG2, under basic conditions (0.1N NaOH) as is known in the art, yields LG3.

c) Product LG4: Product LG3 is reacted with N-hydroxysuccinimide in anhydrous dimethoxyethane solution in the presence of dicyclo-hexylcarbodiimide to obtain LG4 (Anderson G. W. et al. (1964), (21)).

d) Product $^1$LG-P.Al.: Product $^1$LG-P.Al. is reacted with the amino methylester of DL-polyalanine ($H_2N$-

P.Al.-COOMe). in dimethoxyethane solution and in the presence of sodium bicarbonate solution (Anderson G. W. et al. (1964), (21)).

e) Product $^2$LG-P.Al.: The BOC group of $^1$LG-P.Al. is cleaved by trifluoroacetic acid (Trabell D. S. et al. (1972), (22)) to obtain $^2$LG-P.Al.

f) Product $^1$LG-Bis P.Al.: $^2$LG-P.Al. is reacted with the N-hydroxy succinimide of the polyalanine derivative in anhydrous dimethoxyethane solution in the presence of DCC (Anderson G. W. et al. (1964), (21)), to obtain $^1$LG-Bis-P.Al.

g) Product $^2$LG-Bis-P.Al. (free amine): The CBZ protecting group in $^1$LG-Bis-P.Al. is then cleaved by the catalytic transfer by hydrogenation with 1,4 cyclohexadiene in DMF, following the procedure described by Felix A. M. et al (1978), (23), to yield $^2$LG-Bis-P.Al.

1.2 Activation of the silica surface (as epoxide)

An optical fiber (fused silica) having 600 μm core diameter is stripped of approximately 25 mm of cladding. Using (3-glycidoxypropyl) trimethylsilane (GOPS) the quartz core is activated to epoxide and then to aldehyde following the procedure described by Tromberg B. J. and Sepaniak M. J. (1987), (20). The same procedure is used for quartz microscope slide (75×25×2 mm).

1.3 Immobilization of the amino bis-polyalanine derivative ($^2$LG-Bis-P.Al.) to the active surface a) Following the procedure described by Tromberg and Sepaniak (1987), (20), the free amine on the bis-polyalanine derivative ($^2$LG-Bis-P.Al.) is covalently bound to the surface aldehyde, to obtain the immobilized bis-polyalanine spacers, $^1$S-Bis-P.Al. having the formula shown in FIG. 17.

b) Removal of the BOC amino protecting group, to obtain the free amine, is done by using trifluoroacetic acid following the procedure described by Trabell D. S. et al. (1972), (22) to obtain the product $^2$S-Bis-P.Al. having the formula shown in FIG. 18.

EXAMPLE 2

Preparation of the reversible immuno competitive unit for morphine using fluoresceine as the fluorophor (donor) and Rhodamine as the quencher (acceptor).

STRATEGY 2.1—Preparation of Morphine fluoresceine conjugate of the type shown in FIG. 19.

2.2—Coupling of the Morphine-Fluoresceine conjugate to the immobilized bis-polyalanine species (product $^2$S-bis-P.Al.).

2.3—Tagging the specific antibody $^m$F(ab')$_2$ fragments to the quencher.

2.4—Coupling the tagged $^m$F(ab')$_2$ fragments to the sensing surface; production of the complete immuno competitive unit.

2.1 Preparation of Lys.Gly. morphine-fluoresceine conjugate (F-LG3-M)

The preparation includes several steps by using conventional procedures found in the literature. The preparation process is depicted in the scheme of FIG. 20.

a) Product F-LG1: FITC and LG1 (see FIG. 20), are reacted in pyridine/water/triethylamine (11:8:1, v/v/v) solution, under similar conditions as described by McGregor A. R. et al. (1978), (24).

b) Product F-LG2: The amino protecting group (BOC) is cleaved by trifluroacetic acid-H$_2$O under the same conditions as described by Trabell D. S. et al. (1972), (22).

c) Product M3: O$^3$-carboxymethylmorphine is reacted with N-hydroxy-succinimide in anhydrous DMF, and in the presence of dicyclohexyl-carbodiimide (DCC) using the conventional experimental conditions as described by Parini C. et al. (1985), (25).

d) Product F-LG2-M: The activated carboxy group of M3 is reacted with the amine F-LG2 under the similar conditions described by Parini C. et al. (1985), (25).

e) Product F-LG3-M: Saponification of F-LG2-M, under basic conditions (0.1N NaOH), as is well known in the art, yields F-LG3-M.

Figure 21C:
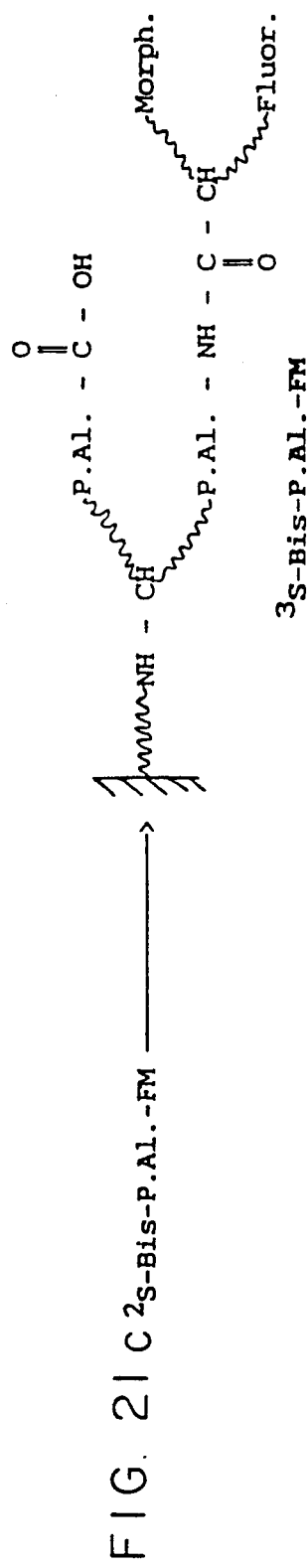
Figure 21D:
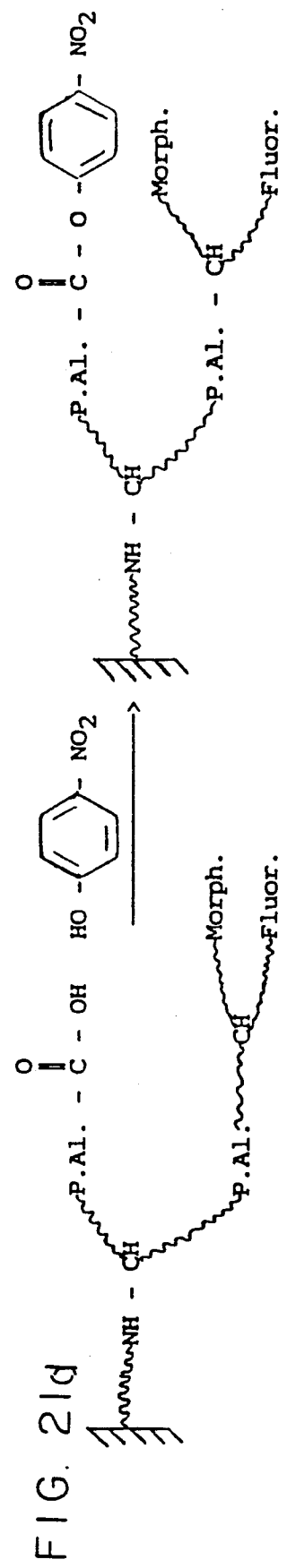

2.2 Coupling of the morphine-Fluoreceine conjugate (F.LG3.M) to the immobilized bis-polyalanine species product $^2$S-Bis-P.Al The coupling process is depicted in the scheme of FIG. 21.

a) Product F-LG4-M: F-LG3-M is reacted with N-hydroxysuccunimide in anhydrous dimethoxyethane solution in the presence of DCC, under conditions described by Anderson G. W. et al. (1964), (21).

b) Product $^2$S-Bis-P.Al.: The activated carboxy group of F-LG4-M is reacted with the amine $^2$S-Bis-P.Al under similar conditions as described by Parini C. et al. (1985), (25), to obtain $^2$S-Bis-P.Al.-FM.

c) Product $^3$S-Bis-P.Al.-FM: Saponification of $^2$S-Bis-P.Al.-FM, under basic conditions (0.1N NaOH), as is well known in the art, yields $^3$S-Bis-P.Al.-FM.

d) Product $^4$S-Bis-P.Al.-FM: The carboxy group of $^3$S-Bis-P.Al.-FM is activated by conversion into the p-nitrophenylester, using DCC as the coupler, following a procedure similar to that described by Bodanszky M. and Vigneaud V. (1959), (26).

2.3 Coupling of the quencher (Rhodamine) to the morphine specific antibody fragments ($^m$F(ab')$_2$), to obtain ($^m$F(ab')$_2$-Rh)

The quencher (Rh2) is cojugated to the $^m$F(ab')$_2$ fragment at room temperature, in acetone solution at pH 9.5 tp 10.0 following a procedure similar to that described by Ullman E. F. et al. 1976), (18), to obtain the product $^m$F(ab')$_2$-Rh.

2.4 Coupling of $^m$F(ab')$_2$-Rh to the sensing surface; producing the complete immuno competitive unit (Product (Rh)$^m$F(ab')$_2$-$^4$S-FM)

The reactions described in this Example are depicted in the reaction schemes of FIG. 22. The coupling is done in two stages:

Product (Rh)$^m$F(ab')$_2$-$^4$S-FM is obtained by incubation of the activated ester product, which includes the labelled morphine ($^4$S-Bis-P.Al.-FM), with a specific immunological reagent, (Rh)$^m$F(ab')$_2$.

The product is obtained in two stages. In the first stage (FIG. 22 (a)) $^4$S-FM ‖ ‖ ‖ $^m$F(ab')$_2$(Rh), which is an immuno-affinity conjugate, is obtained. In the second stage (scheme 2.4(b)) the amino group of $^m$F(ab')$_2$ interacts with the activated carboxy to produce the amide bond by which the (Rh)$^m$F(ab')$_2$ is covalently bound to the polyalanine spacer. In the product of this stage, (Rh)$^m$F(ab')$_2$-$^4$S-FM, the immuno components ((Rh)$^m$F(ab')$_2$ and the immobilized morphine) are kept conjugated by affinity interaction.

The incubation is carried out for a period of about 1 h in a solution of DMF and trimethylamine (Bodansky M. and Vigneaud V. (1959), (26)). The product is then washed with phosphate buffer solution, pH 8.0, and is kept in cold (4° C.) until used.

EXAMPLE 3

Preparation of the reversible immuno competitive unit for HSA, using Texas-Red as the fluorescent label.

STRATEGY 3.1—Preparation of the labelled HSA (labelled with Texas-Red).

3.2—Immobilization of $^{HSA}F(ab')_2$ fragments to the sensing surfaces.

3.3—Covalent binding of the labelled HSA to the polyalanine spacer; production of the complete immuno competitive unit.
  (a)-Conjugation of the labeled HSA to the immobilized $^{HSA}F(ab')_2$, by affinity interaction.
  (b)-Covalent binding of the affinity conjugated HSA to the polyalanine spacer; production of the complete immuno competitive unit.

3.1 Preparation of HSA-Texas-Red conjugate

The reaction is depicted in FIG. 23.

The procedure is similar to that described by Chan M.A. et al. (1987) Ref. 27. Five mg HSA are dissolved in 30 ml of 0.1 mol/l carbonate buffer (pH 9.1). Seven mg Texas Red sulfonylchloride solution (dissolved in 200 µl of DMF) is added (while stirring) at room temperature, for one hour. The reaction mixture is then dialyzed three times against 5 liters of 0.1 mol/l NaCO$_3$ solution, containing 0.25 g sodium azide per liter.

Figures 24C, 24D:
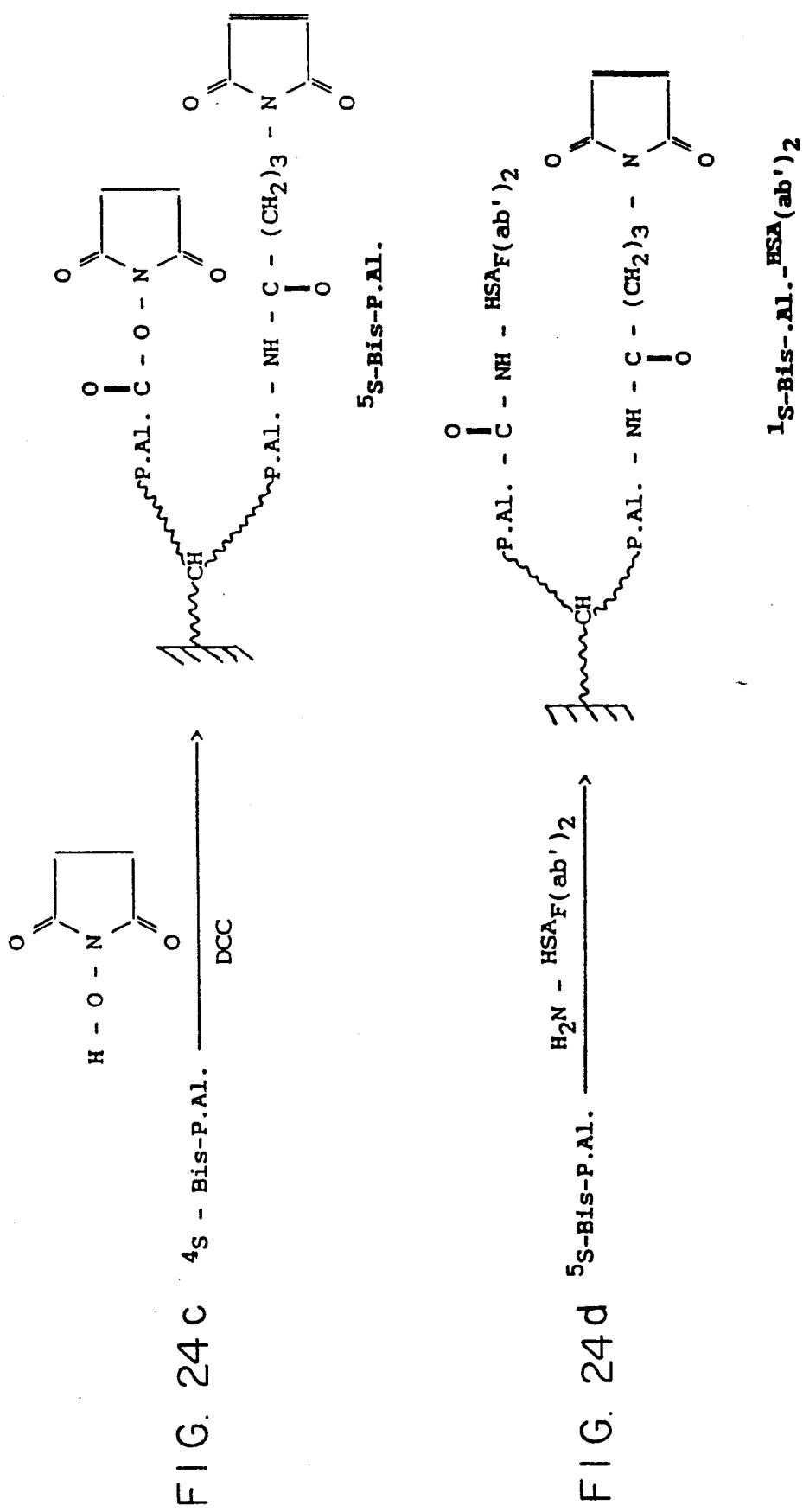

3.2 Immobilization of $^{HSA}F(ab')_2$ fragments to the immobilized bis-polyalanine The procedure is depicted in the scheme of FIG. 24.

a) Product $^3$S-Bis-P.Al.:Saponification of $^2$S-Bis-P.Al. under basic conditions (0.1N NaOH) as is well known in the art, yields product $^3$S-Bis-P.Al.

b) Product $^4$S-Bis-P.Al.: This activated product is obtained by interaction of product $^3$S-Bis-P.Al. with the hetrobifunctional reagent N-hydroxysuccinimide ester of N-(4-carboxycyclohexyl methyl)-maleimide) The reaction is carried out in sodium phosphate buffer (0.1 M, pH 7.5) in DMF solution, under conditions similar to those described by Claassen et al. (1986), (28).

The amino group on the derivitized silica ($^2$S-Bis-P.Al.) is reacted with succinimidyl 4-maleimidylbutyrate in 0.1 M sodium phosphate buffer, pH 7.0 at 30° C. Reaction condition are similar to those described for proteins (Claassen E. et al. (1986), (28)).

c) Product $^4$S-Bis-P.Al.: The carboxy group in $^3$S-Bis-P.Al. is activated by N-hydroxysuccinimide in DMF solution, under conditions similar to those described by Anderson G. W. et al. (1964), (21).

d) Product $^1$S-Bis-P.Al-$^{HSA}$F(ab')$_2$: The $^{HSA}$F(ab')$_2$ is covalently bound to the derivatized active surface ($^4$S-Bis-P.Al.) in PBS solution, pH 7.4, using conditions similar to those described by Claassen E. et al (1986), (28).

Figure 25A:
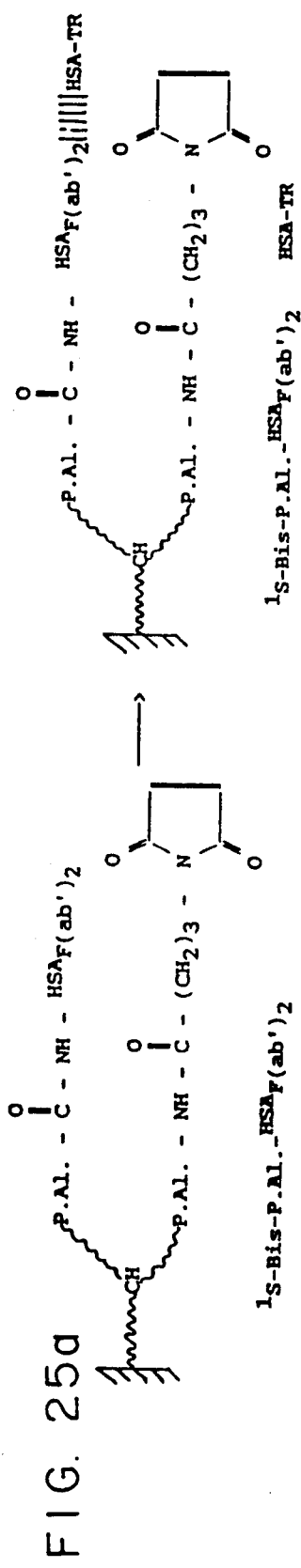
Figure 25B:
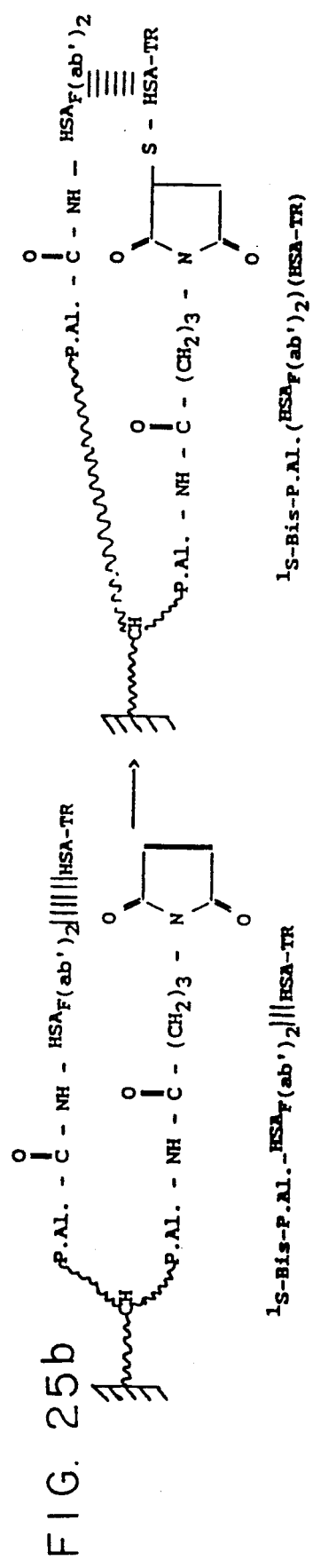

3.3 Immobilization of the labelled HSA to the polyalanine spacer:Preparation of the immobilized immuno competitive unit ($^1$S-Bis-P.Al.($^{HSA}$F(ab')$_2$)(HSA-TR)). The procedure is depicted in the scheme of FIG. 25.

Product $^1$S-Bis-P.Al.($^{HSA}$F(ab')$_2$)(HSA-TR): This product is obtained by incubation of the activated maleimide product $^1$S-Bis-P.Al.$^{HSA}$F(ab')$_2$ with the labelled HSA, (HSA-TR), in two stages in sodium phosphate buffer (0.1 M, pH 7.5). In the first stage which is carried out at room temperature for 1 h (FIG. 25 (a)), $^1$S-Bis-P.Al.-$^{HSA}$F(ab')$_2$ ‖ ‖ ‖ HSA-TR is obtained which is an immuno-affinity conjugate. In the second stage which is carried out at 4° C. for 24 h (FIG. 25 (b)), the labelled HSA is bound covalently to the polyalanine spacer by interaction between the HSA thiol group and maleimide. The product $^1$S-Bis-P.Al. $^{HSA}$F(ab')$_2$(HSA-TR) is well washed in PBS solution and kept at 4° C. until use.

EXAMPLE 4

Figure 26:
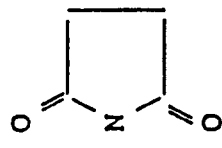

Preparation of immobilized immuno competitive unit for HSA, based on StAv-Biotin affinity interaction as depicted in FIG. 26.

Strategy 4.1—Immobilization of Streptavidin (StAv) on the silica surface)

4.2—Preparation of Biotinylated HSA-fluor.

4.3—Preparation of Biotinylated $^{HSA}$F(ab')$_2$-Rh.

4.4—Preparation of the Biotinylated type FIG. 2(d); immuno competitive unit for HSA (conjugate Rh-F(ab')$_2$ HSA-fluor.).

4.5—Immobilization of the Bis-biotinylated immuno competitive unit to the surface (via StAv).

4.1 Immobilizatio Streptavidin on the silica surface

Figure 27A:
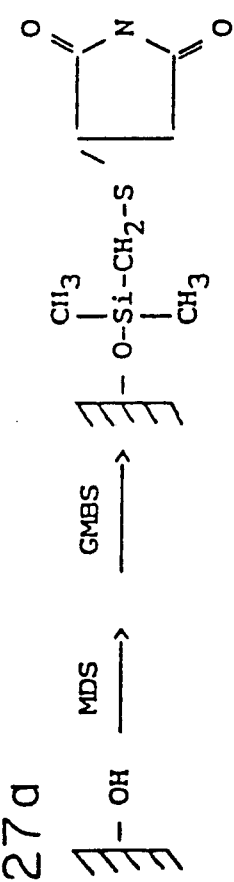
Figure 27B:
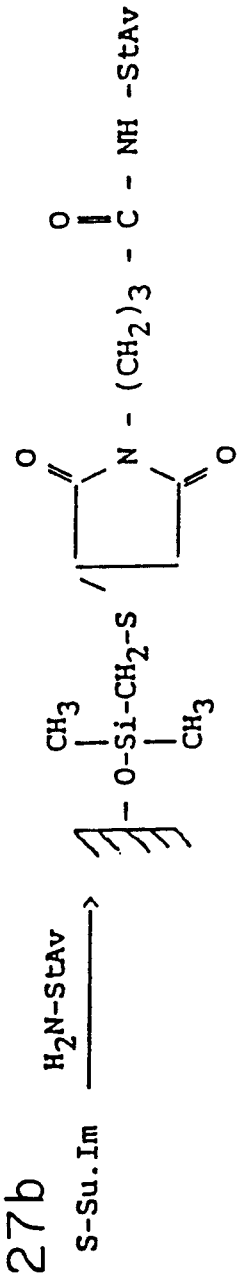

The procedure is depicted in the scheme of FIG. 27.

Procedures a) Activation of the silica surface

A fiber (fused silica) having 600 µm core diameter is stripped of approximately 25 mm of cladding. The activation of the silica surface is done by MDS and GMBS following the procedure described by Bhatia et al (1989), (29).

b) Immobilization of StAv

A solution of the StAv in PBS is placed on silica coated with silane and a crosslinker (S-Su.Im.) and allowed to incubate for 1 h, at room temperature under conditions similar to those described by Bhatia et al (1989), (29), to obtain S-StAv.

4.2 Preparation of biotinylated HSA-F1

Figure 28C:
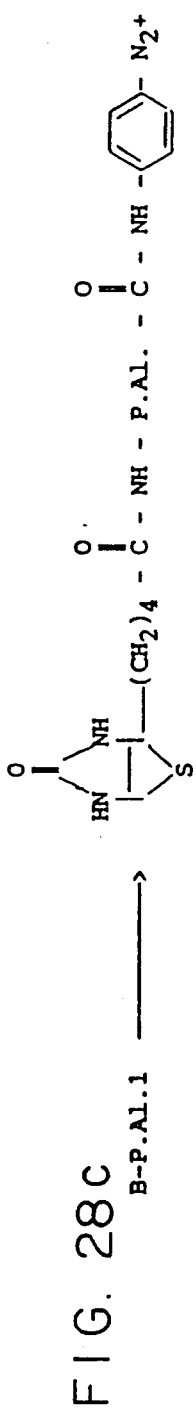
Figure 28D:
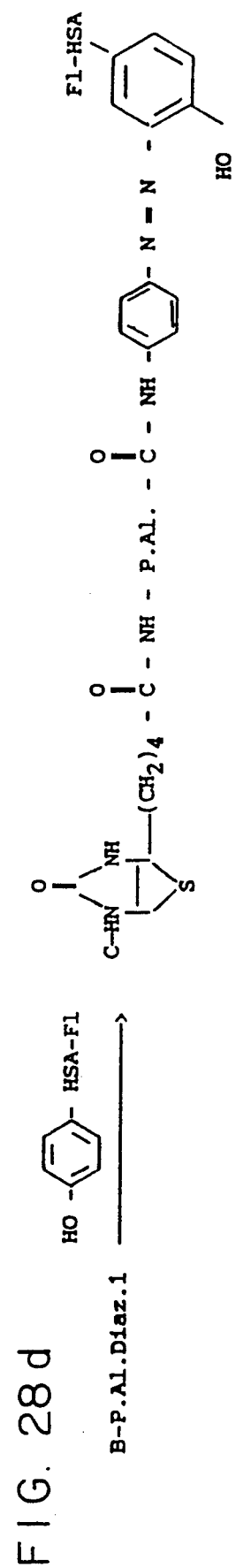

The procedure is depicted in the scheme of FIG. 28
a) Product HSA-F1: 4'-5'-Dimethoxy-5(and 6) carboxyfluoresceine-N-hydroxy succinimide ester, is reacted with HSA in phosphate buffer, pH 8.0, under experimental conditions, similar to those described by Khanna and Ullman (1980), (7).

b) Product B-P.Al.: The product is obtained by the conventional procedure of condensation between the activated biotin and the amine group of the polyalanine (Anderson et al. (1964), (21).

c) Product B-P.Al.-diazl: This biotin derivative is prepared by a procedure similar to those described by Bayer E. A. and Wilchek M. (1980), (30).

d) Product B-P.Al.-HSA-F(ab')$_2$: B-P.Al.-diaz.1 freshly prepared (just before use) is added to the labelled HSA (HSA-F1) in PBS solution (pH 7.5) and incubated for 1 h at room temperature, to get B-P.Al.-

HSA-F1. The reaction is based on the interaction of tyrosine groups, present on the HSA protein, and the diazo reagent-(Bayer E. A. and Wilchek M. (1980), (30)).

4.3 Preparation of biotinylated $^{HSA}F(ab')_2$-Rh

Figure 29A:
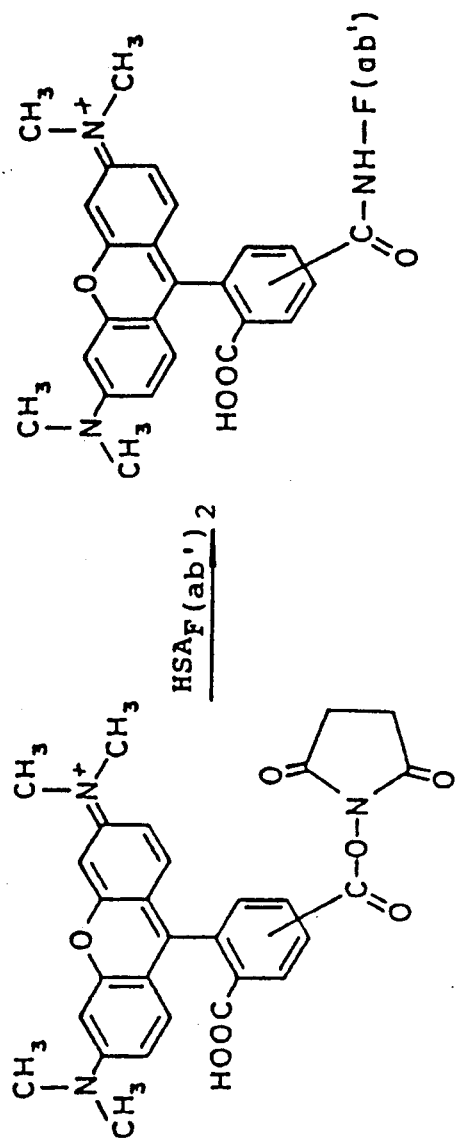
Figure 29B:
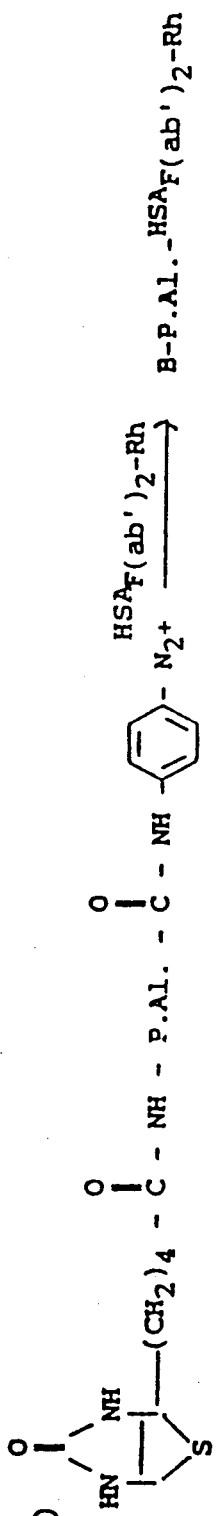

The procedure is depicted in the scheme of FIG. 29.

a) $^{HSA}F(ab')_2Rh$: N,N,N', N'-tetramethylrhodamine-6-carboxylic acid NHS ester is reacted with $^{HSA}F(ab')_2$ in phosphate buffer, pH 8.0 under conditions similar to those described by Khanna and Ullman (1980), (7).

b) B-P.Al.-$^{HSA}F(ab')_2$-Rh: This product is obtained by reacting the labelled specific antibody $^{HSA}F(ab')_2$ fragment with the freshly prepared diazo reagent (Bayer E. A. and Wilchek (1980), (30)).

4.4 Preparation of bis-biotinylated immuno competitive unit for HSA (conjugate B-(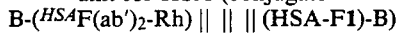

The product is obtained by incubation of the two biotinylated immunological reagents, B-P.Al-$^{HSA}F(ab')_2$-Rh and B-P.Al.-HSA-F1. in PBS solution (pH 8.0) for 1 h at room temperature) Schematic description of this affinity interaction is depicted in FIG. 30.

4.5 Immobilization of the biotinylated HSA immuno competitive unit on the surface The reaction is depicted in FIG. 31.

Procedure

The StAv substrate (a silica fiber or a microscope slide) is incubated for 1 h, in phosphate buffer solution (pH 8.0), with the biotinylated immuno competitive conjugate (B-($^{HSA}F(ab')_2$-Rh) || || || (HSA-F1)-B) to produce the product: (F1)HSA-B || || || StAv || || || B-$^{HSA}F(ab')_2$(Rh).

EXAMPLE 5

Reversible biosensor of morphine

An optical fiber is treated as described in Example 1.2 and a morphine immuno competitive unit is immobilized thereon as described in Example 2. The surface capacity on the fiber core (600 μm diameter, 25 mm long) is of the order of about $3 \times 10^{-12}$ mole of morphine immuno competitive units (morph.-ICU). The monitoring conditions of morphine on the biosensor, depends on the fluorescence energy transfer technique. The immuno competitive units in this system are (Rh)$^m$F(ab')$_2$-4S-FM as described in Example 2 and they contain labelled fluorescent morphine with fluoresceine as the donor, and (Rh)$^m$F(ab')$_2$ with rhodamine as acceptor (quencher).

FIG. 12 shows a schematic presentation of the sensing system. In this case argon laser is directed into the fiber, through the 490 nm laser line filter, to excite the immobilized fluoresceine, and fluorescence is detected at 520 nm.

All the morphine measurements are carried out in phosphate buffer (0.01 M, pH 7.5) which is prepared from NaH$_2$PO$_4$ and Na$_2$HPO$_4$, containing 1% sodium chloride and 0.1% sodium azide as a preservative. The fluorescence signal of the buffer (background) is substracted from all measurements.

EXAMPLE 6

Reversible biosensor for human serum albumin (HSA)

The immuno competitive product for HSA described in Example 4.5, (F1)HSA-B || || || StAv || || || B-$^{HSA}F(ab')_2$(Rh), is immobilized on an optical fiber as described in Examples 1.

The surface capacity on the fiber core (600 μm diameter, 25 mm long) is determined to be $2.10 \times 10^{-12}$ mole of the HSA immuno competitive units (HSA-ICU).

The continuous monitoring of HSA, with this biosensor, also relies on the fluorescence energy transfer technique. The immuno competitive unit contains 4,5-dimethoxy-5-(and -6-) carboxyfluorescein labelled HSA, which acts as the energy donor, and N,N,N',N',-tetramethylrhodamine-6-carboxyrhodamine, labelled $^{HSA}F(ab')_2$ wherein the rhodamine derivative acts as the acceptor (quencher).

The optical detection system is again as schematically shown in FIG. 12, i.e. the same as in Example 5 ($\lambda_{excitation}$ —490; $\lambda_{emission}$ —520 nm). All measurements of HSA standard solutions are carried out in phosphate buffer (0.01 M, pH 7.5), which is prepared from NaH$_2$PO$_4$ and Na$_2$HPO$_4$, containing 1% sodium chloride and 0.1% sodium azide as a preservative.

I claim:

1. An analyte-specific chemical sensor for determining an analyte in a test medium, comprising a carrier body with a sensing surface having attached thereto a plurality of reversible competitive recognition units, called, RCRUs each comprising as constituent components at least one bound receptor and one bound ligand arranged in such relationship that in the absence of analyte the receptor or receptors and the ligand or ligands of each RCRU associate to form a conjugate, which conjugate competitively disassociates in the presence of the analyte said receptor and ligand remaining bound to said surface and reassociate when the analyte concentration in the test medium is decreased; wherein at least one detectable physico-chemical property of the RCRU is modulated by fluctuations of the analyte concentration as a correlate of the dissociation and reassociation of the components of the RCRU.

2. A sensor according to claim 1, wherein the constituent components of each RCRU are bound directly to the sensing surface.

3. A sensor according to claim 1 wherein the constituent components of each RCRU are bound to the sensing surface via at least one spacer molecule.

4. A sensor according to claim 3, wherein each of the constituent components of each RCRUs is linked to the sensing surface separately via its own spacer molecule.

5. A sensor according to claim 3, wherein said constituent components of each RCRUs are interconnected by a common spacer molecule to form a molecular construct with receptor and ligand moieties, which construct is linked to the sensing surface.

6. A sensor according to claim 5, wherein said construct is linked directly to the sensing surface.

7. A sensor according to claim 5, wherein said construct is linked to the sensing surface by means of a spacer molecule.

8. A sensor according to claim 1, wherein the constituent components of the RCRU are complementary participants in an immunogenic type reaction and are selected from the groups of antibodies and antigens.

9. An apparatus for continuously measuring the concentration of an analyte in liquid or gaseous phase, comprising a probing vessel fitted with a sensor according to claim 1, and at least one transducer which transduces receptor-ligand association and dissociation into at least one measurable physico-chemical phenomenon.

10. Apparatus according to claim 9 designed as a monitor for continuous operation, wherein said probing vessel is adapted for the continuous throughflow of a liquid or gaseous test fluid.

11. An apparatus according to claim 9, wherein the detected physico-chemical phenomenon is optical, electrochemical or piezoelectrical.

12. An analyte-specific chemical sensor for determining an analyte in a test medium, comprising a carrier body with a sensing surface having attached thereto a plurality of reversible competitive recognition units, called, RCRUs each comprising as constituent components at least one bound receptor and one bound ligand arranged in such relationship that in the absence of analyte the receptor or receptors and the ligand or ligands of each RCRU associate to form a conjugate, which conjugate competitively disassociates in the presence of the analyte, said receptor and ligand remaining bound to said surface, and reassociates when the analyte concentration in the test medium is decreased; wherein each of either of the constituent receptor or receptors and ligand or ligands of the RCRU bears a labelling group at least one detectable physico-chemical property of which is modulated by fluctuations of the analyte concentration as a correlate of the dissociation and reassociation of the components of the RCRU.

13. A sensor according to claim 12 wherein said labelling group manifests an optical activity which is reversibly modulated by fluctuations of the analyte concentration in the test medium.

14. A sensor according to claim 12, wherein each of either of the said receptor or receptors and ligand or ligands of each RCRU is a recognizer and the other is an analyte analogue bearing a luminophore group producing upon excitation a luminescence which is modulated by fluctuations of the analyte concentration in the test medium.

15. A sensor according to claim 14, wherein the sensor body is a waveguide and the analyte analogue is excited by an evanescent light wave propagating at the interface between said waveguide and a liquid or gaseous test fluid.

16. A sensor according to claim 15, wherein said waveguide is designed to conduct the luminescence emitted by the labelled analyte analogue.

17. A sensor according to claim 15, wherein said waveguide is an optical fibre having an unclad sensing portion coated with RCRUs.

18. A sensor according to claim 15, wherein said waveguide is a flat body having at least one face coated with RCRUs.

19. A sensor according to claim 16, wherein the labelled analyte analogue emits a polarized luminescence is modulated by fluctuations of the analyte concentration in the test medium.

20. A sensor according to claim 14, wherein each recognizer bears a quencher group which upon formation of said inner conjugate suppresses the luminescence of the analyte analogue, which luminescence increases upon dissociation of said inner conjugate.

21. A sensor according to claim 14, wherein each recognizer bears an enhancer group which upon formation of said inner conjugate enhances the luminescence of the analyte analogue, which luminescence increases upon dissociation of said inner conjugate.

22. A sensor according to claim 12 wherein said labelling group manifests an electrochemical activity which is modulated by fluctuations of the analyte concentration in the test medium.

23. A sensor according to claim 22, wherein the carrier body is an electrode.

24. A sensor according to claim 22, wherein the carrier body is a field effect transistor.

25. A sensor according to claim 12, wherein the the carrier body is a piezoelectric transducer the frequency of which is modulated by the fluctuations of the analyte concentration.

* * * * *